(12) United States Patent
Li et al.

(10) Patent No.: US 9,066,979 B2
(45) Date of Patent: Jun. 30, 2015

(54) QUINAZOLINE INHIBITORS OF ACTIVATING MUTANT FORMS OF EPIDERMAL GROWTH FACTOR RECEPTOR

(71) Applicant: ASTRAZENECA AB, Södertälje (SE)

(72) Inventors: David Yunzhi Li, Shanghai (CN); Jiabing Wang, Shanghai (CN); Zhenfan Yang, Shanghai (CN); Qingbei Zeng, Shanghai (CN); Xiaolin Zhang, Shanghai (CN)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 14/197,476

(22) Filed: Mar. 5, 2014

(65) Prior Publication Data

US 2014/0255428 A1    Sep. 11, 2014

(30) Foreign Application Priority Data

Mar. 6, 2013    (WO) ................ PCT/CN2013/072250

(51) Int. Cl.
| | | |
|---|---|---|
| *C07D 403/12* | (2006.01) | |
| *A61K 31/517* | (2006.01) | |
| *A61K 45/06* | (2006.01) | |
| *A61K 31/4184* | (2006.01) | |
| *A61K 31/4985* | (2006.01) | |
| *A61K 31/519* | (2006.01) | |

(52) U.S. Cl.
CPC ............. *A61K 45/06* (2013.01); *C07D 403/12* (2013.01); *A61K 31/517* (2013.01); *A61K 31/4184* (2013.01); *A61K 31/4985* (2013.01); *A61K 31/519* (2013.01)

(58) Field of Classification Search
None
See application file for complete search history.

(56) References Cited

U.S. PATENT DOCUMENTS

| | | | |
|---|---|---|---|
| 5,457,105 A | 10/1995 | Barker et al. | |
| 8,648,087 B2* | 2/2014 | Lyssikatos et al. ........ | 514/266.1 |
| 2002/0082271 A1 | 6/2002 | Himmelsbach et al. | |
| 2008/0167328 A1 | 7/2008 | Huang et al. | |
| 2008/0177068 A1 | 7/2008 | Huang et al. | |
| 2010/0234371 A1 | 9/2010 | Himmelsbach et al. | |

FOREIGN PATENT DOCUMENTS

| | | |
|---|---|---|
| CN | 101367793 A | 2/2009 |
| CN | 101857618 A | 10/2010 |
| WO | WO 96/33980 A1 | 10/1996 |
| WO | WO 97/30034 A1 | 8/1997 |
| WO | WO 97/38994 A1 | 10/1997 |
| WO | WO 00/55141 A1 | 9/2000 |
| WO | WO 01/21594 A1 | 3/2001 |
| WO | WO 02/18351 A1 | 3/2002 |
| WO | WO 03/082831 A1 | 10/2003 |
| WO | WO 2005/012290 A1 | 2/2005 |
| WO | WO 2005/026156 A1 | 3/2005 |
| WO | WO 2005/028469 A1 | 3/2005 |
| WO | WO 2005/028470 A1 | 3/2005 |
| WO | WO 2005/097134 A2 | 10/2005 |
| WO | WO 2005/097137 A2 | 10/2005 |
| WO | WO 2007/023073 A2 | 3/2007 |
| WO | WO 2007/059257 A2 | 5/2007 |
| WO | WO 2010/061208 A2 | 6/2010 |
| WO | WO 2011/021212 A1 | 2/2011 |

OTHER PUBLICATIONS

Voskoglou-Nomikos et al., Clinical predictive value of the in vitro cell line, human xenograft, and mouse allograft preclinical cancer models, National Cancer Institute of Canada Clinical Trials Group et al.. 2003. vol. 9. pp. 4227-4239.*
Cancer Drug Design and Discovery, Neidle, Stephen,ed. (Elsevier/Academic Press), pp. 427-431 (2008).*
Zukin Rev.Assoc.Med. Bras. vol. 58, pp. 263-268 (2012).*
Galvani et al. Current Pharmaceutical Design vol. 19, pp. 818-832 (2013).*
Barnholtz-Sloan et al; Incidence Proportions of Brain Metastases in Patients Diagnosed (1973 to 2001) in the Metropolitan Detroit Cancer Surveillance System; Journal of Clinical Oncology; 2004; p. 2865-2872; 22(14).
Bartolotti et al; EGR receptor tyrosine kinase inhibitors in the treatment of brain metastases from non-smal-cell lung cancer; Expert Rev Anticancer Ther; 2012; p. 1429-1435; 12(11).
Gavrilovic et al; Brain metastases: epidemiology and pathophysiology; Journal of Neuro-Oncology; 2005; p. 5-14; 75.
Grommes et al; "Pulsatile" high-dose weekly erlotinib for CNS metastases from EGFR mutant non-small cell lung cancer; Neuro-Oncology; 2011; p. 1364-1369; 13(12).

(Continued)

*Primary Examiner* — Emily Bernhardt

(57) ABSTRACT

The invention relates to compounds of formula (I), or a pharmaceutically acceptable salt thereof:

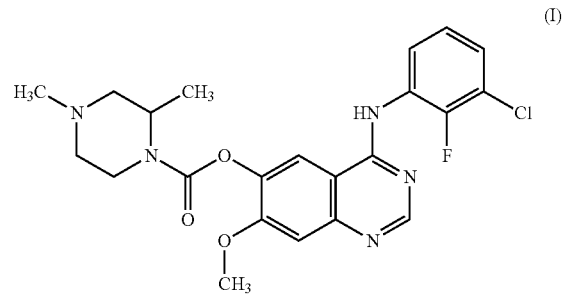

(I)

which possess inhibitory activity against activating mutant forms of EGFR, and are accordingly useful for their anti-cancer activity and in methods of treatment of the human or animal body. The invention also relates pharmaceutical compositions containing them and to their use in the manufacture of medicaments of use in the production of an anti-cancer effect in a warm-blooded animal such as man.

16 Claims, 12 Drawing Sheets

(56) References Cited

OTHER PUBLICATIONS

Jackman et al; Response and Resistance in a Non-Small-Cell Lung Cancer Patient With an Epidermal Growth Factor Receptor Mutation and Leptomeningeal Metastases Treated With High-Dose Gefitinib; Journal of Clinical Oncology; 2006; p. 4517-4520; 24.

Li et al; Novel EGFR inhibitors prepared by combination of dithiocarbamic acid esters and 4-anilinoquinazolines; Bioorganic & Medicinal Chem Lett; 2011; p. 3637-3640; 21.

McKillop et al; In vitro metabolism of gefitinib in human liver microsomes; Xenobiotica; 2004; p. 983-1000; 34 (11-12).

Mok et al; Gefitinib or Carboplatin-Paclitaxel in Pulmonary Adenocarcinoma; The New England Journal of Medicine; 2009; p. 947-957; 361 (10).

Schouten et al; Incidence of Brain Metastases in a Cohort of Patients with Carcinoma of the Breast, Colon, Kidney, and Lung and Melanoma; Cancer; 2002; p. 2698-2705; 94.

Zhou et al; Erlotinib versus chemotherapy as first-line treatment for patients with advanced EGFR mutation-positive non-small-cell lung cancer (Optimal, CTONG-0802): a multicentre, open-label, randomised, phase 3 study; Lancet Oncol; 2011; p. 735-742; 12.

\* cited by examiner

Figure 2:
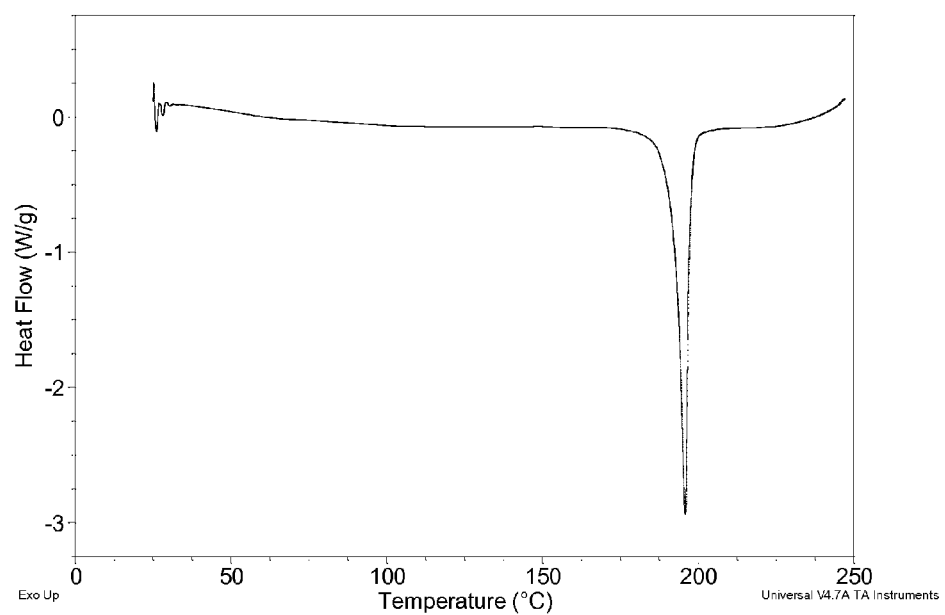

Figure 2: DSC Thermogram Form A

Figure 4:
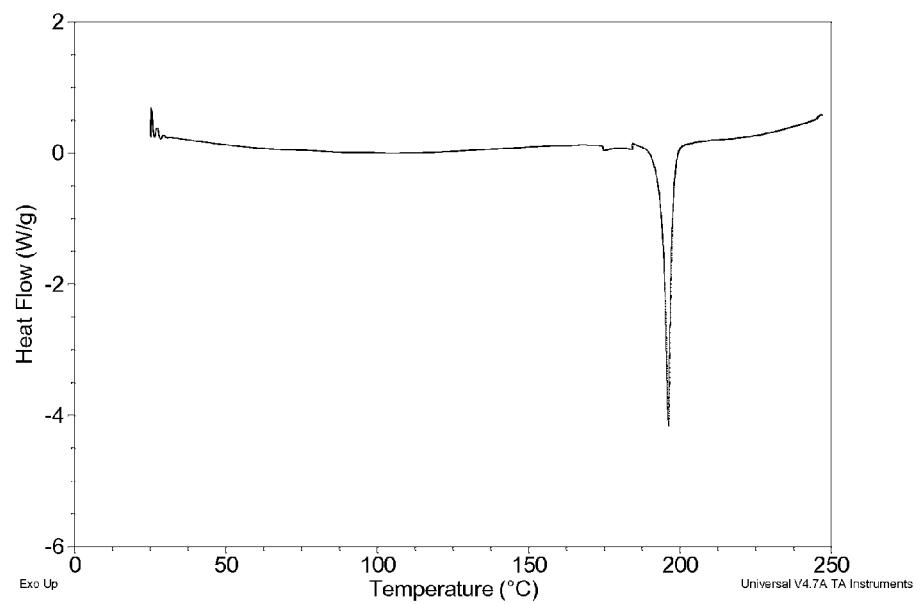

Figure 4: DSC Thermogram Form E

Figure 6:
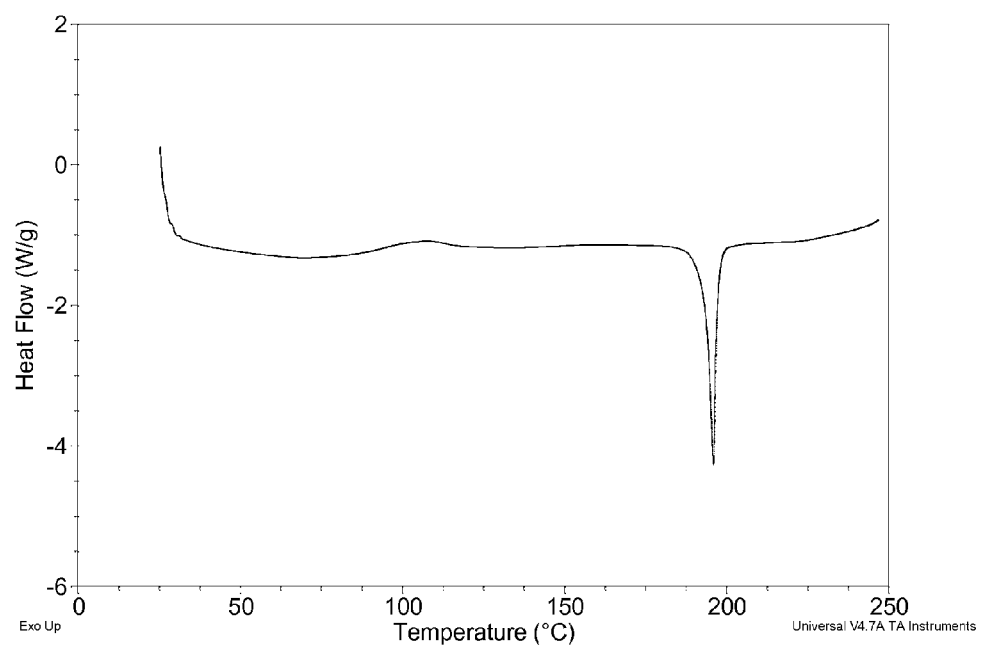

Figure 6: DSC Thermogram Form I

Figure 8:
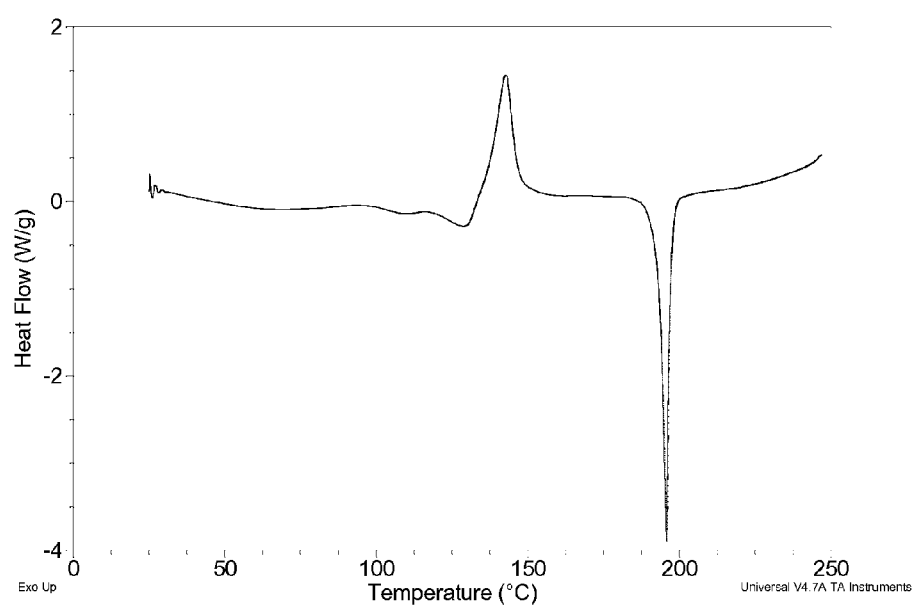

Figure 8: DSC Thermogram Form J

Figure 10: DSC Thermogram mono-HCl salt A₁
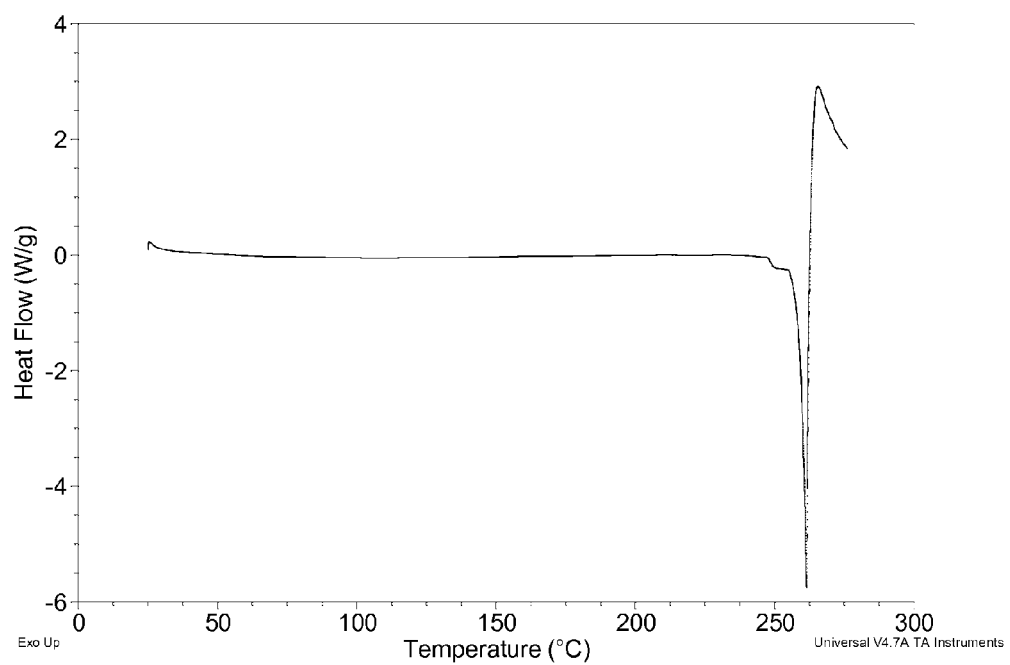

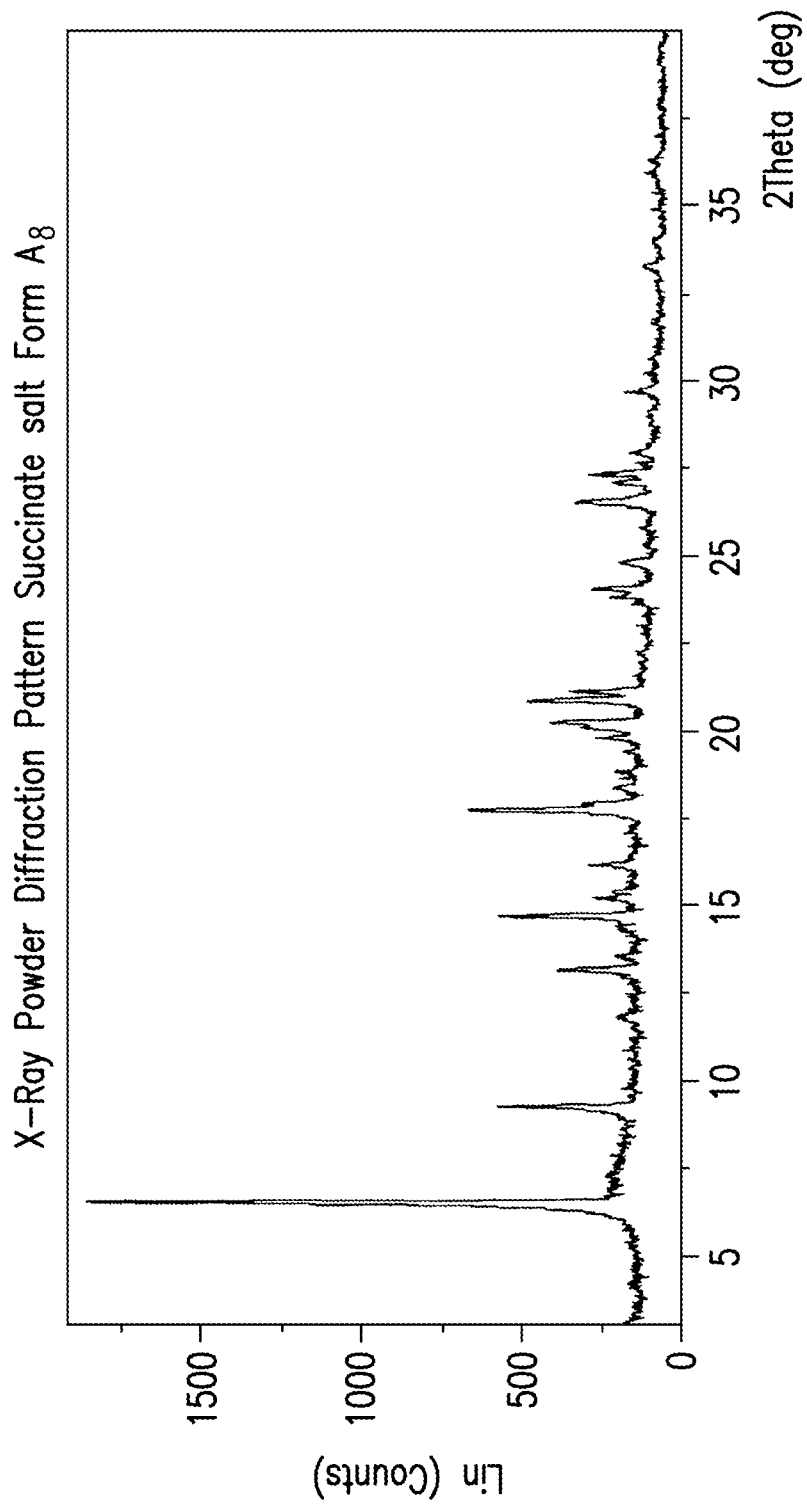

Figure 12: DSC Thermogram Succinate salt Form A$_8$
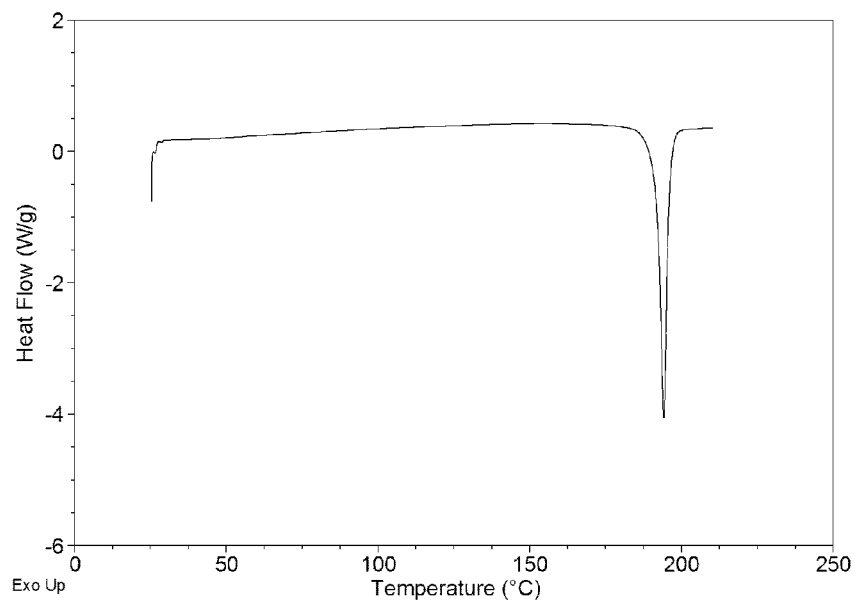

QUINAZOLINE INHIBITORS OF ACTIVATING MUTANT FORMS OF EPIDERMAL GROWTH FACTOR RECEPTOR

RELATED APPLICATIONS

This application claims priority under 35 U.S.C. §119(a) (Pre-AIA) to International Application No. PCT/CN2013/072250, filed Mar. 6, 2013. The contents of the foregoing application are hereby incorporated in their entirety.

The present invention relates to certain 4-(substituted-anilino)-6-O-(substituted-piperizine-carbonyl)quinazoline compounds and pharmaceutically salts thereof which may be useful in the treatment or prevention of a disease or medical condition mediated through activating mutant forms of epidermal growth factor receptor (EGFR), for example the L858R activating mutant and/or the Exon 19 deletion activating mutants. Such compounds and salts thereof may be useful in the treatment or prevention of a number of different cancers. The invention also relates to pharmaceutical compositions comprising said compounds, or a pharmaceutically salt thereof, crystalline forms of these compounds, or a pharmaceutically salt thereof, intermediates useful in the manufacture of said compounds, or a pharmaceutically salt thereof, and to methods of treatment of diseases mediated by activating mutant forms of EGFR using said compounds, or a pharmaceutically salt thereof.

EGFR (otherwise known as ErbB1 or HER1) is a transmembrane protein tyrosine kinase member of the erbB receptor family. Upon binding of a growth factor ligand such as epidermal growth factor (EGF), the receptor can homo-dimerise with another EGFR molecule or hetero-dimerise with another family member such as erbB2 (HER2), erbB3 (HER3), or erbB4 (HER4).

Homo- and/or hetero-dimerisation of erbB receptors results in the phosphorylation of key tyrosine residues in the intracellular domain and leads to the stimulation of numerous intracellular signal transduction pathways involved in cell proliferation and survival. Deregulation of erbB family signalling promotes proliferation, invasion, metastasis, angiogenesis, and tumour cell survival and has been described in many human cancers, including those of the lung, head and neck and breast.

The erbB family therefore represents a rational target for anticancer drug development and a number of agents targeting EGFR or erbB2 are now clinically available, including gefitinib (IRESSA™), erlotinib (TARCEVA™) and lapatinib (TYKERB™, TYVERB™). Detailed reviews of erbB receptor signalling and its involvement in tumourigenesis are provided in *New England Journal of Medicine* [2008] Vol. 358; 1160-74 and *Biochemical and Biophysical Research Communications* [2004] Vol. 319: 1-11.

In 2004 it was reported (*Science* [2004] Vol. 304: 1497-500 and *New England Journal of Medicine* [2004] Vol. 350; 2129-39) that activating mutations in EGFR correlated with response to gefitinib therapy in non-small-cell lung cancer (NSCLC). Approximately 90% of NSCLC associated EGFR mutations consist of two major EGFR mutations (E746-A750del in Exon 19 and L858R substitution mutation in Exon 21) (Pao et al. *Proceedings of the National Academy of Sciences of the United States of America* [2004], Vol. 13: 306-11 and Kosada et al. *Cancer Research* [2004] Vol. 64: 8919-23). These activating mutations, result in an increase in affinity for small molecule tyrosine kinase inhibitors such as gefitinib and erlotinib and a decrease in affinity for adenosine triphosphate (ATP) relative to wild type (WT) EGFR.

However, adverse effects, such as skin rash and diarrhoea, which are considered to be related to inhibition of WT EGFR signalling pathways in normal skin and gut cells, were reported in >60% NSCLC patients treated with gefitinib or erlotinib (Zhou C C et al. *Journal of Clinical Oncology* [2011], Vol. 12: 735-42; Mok T S et al. *New England Journal of Medicine* [2009], Vol. 361: 947-57). In addition, both gefitinib and erlotinib showed limited effects on treating NSCLC patients with brain metastasis, since neither of them effectively cross the blood-brain-barrier (BBB) (McKillop D et al. *Xenobiotica* [2004], Vol. 34: 983-1000; Jackman D M et al. *Journal of Clinical Oncology* [2006], Vol. 24: 4517-20 Grommes C et al. *Neuro-Oncology* [2011], Vol. 13: 1364-9), while several reports show that lung cancer brain metastasis are emerging as an unmet medical need (Gavrilovic et al, *Journal of Neurooncology* [2005], Vol. 75: 5-14; Barnholtz-Sloan J S et al. *Journal of Clinical Oncology* [2004], 22: 2865-72; Schouten L J et al, *Cancer* [2002], Vol. 94: 2698-705).

Leptomeningeal metastases occur when cancer spreads to the meninges, the layers of tissue that cover the brain and the spinal cord. Metastases can spread to the meninges through the blood or they can travel from brain metastases, carried by the cerebrospinal fluid (CSF) that flows through the meninges. If tumour cells enter the CSF and survive, they can travel throughout the central nervous system, causing neurological problems (Le Rhun et al. *Surg Neurol Int*. [2013], Vol. 4: S265-88). The incidence of leptomeningeal metastases is increasing, partly because cancer patients are living longer, but also because many chemotherapies and molecular target therapies are unable to reach sufficient concentrations in the cerebral spinal fluid to kill the tumour cells. Treatments have traditionally been ineffective and survival has been measured in weeks.

AstraZeneca has investigated sapitinib (AZD8931), an equipotent inhibitor of EGFR, HER2 and HER3 receptors, for use in breast cancer. To date sapitinib has been studied in three phase II clinical trials; the first in combination with paclitaxel versus paclitaxel alone in advanced breast cancer patients expressing low levels of HER2; the second in combination with anastrozole versus anastrozole alone in hormone receptor positive advanced breast cancer; and the third in combination with paclitaxel versus paclitaxel alone in metastatic, gastric or gastro-oesophageal junction cancer who progress following first line therapy and are ineligible for treatment with trastuzumab by HER2 status. The compound of the present invention is structurally distinct from sapitinib, and possesses enhanced brain penetration properties which make it potentially useful in the treatment of cancers that have metastasised to the central nervous system [CNS], particularly those that have metastasised to the brain and those that result in leptomeningeal metastases.

Currently some irreversible quinazoline EGFR inhibitors, such as afatinib and dacomitinib, are under clinical development. Although these compounds showed comparable effects on EGFR activating mutations in NSCLC patients with gefitinib and erlotinib, they demonstrated more severe adverse effects, such as skin rash (>90% skin rash and diarrhoea) (Zhou C C et al. *Journal of Clinical Oncology* [2011], Vol. 12: 735-42; Mok T S et al. *New England Journal of Medicine* [2009], Vol. 361: 947-57; Miller V A et al. *Lancet Oncology* [2012], Vol. 13: 528-38; Ramalingam S S et al. *Journal of Clinical Oncology* [2012], Vol. 30: 3337-44). The compounds of the present invention are reversible inhibitors, and are therefore expected to have less EGFR-related adverse effects than afatinib and dacomitinib.

Certain quinazoline compounds have been disclosed, e.g. "Preparation of quinazoline derivatives for treatment of tumors" (US 20080177068 A1), "Preparation of quinazoline derivatives for treatment of tumors" (US 20080167328 A1), "Preparation of saccharide derivatives of quinazolines as protein tyrosine kinase inhibitors" (CN 101857618 A), "Preparation of chlorofluoroanilinomethoxy-N-methylcarbamoyl-methylpiperidinyloxyquinazoline derivatives for use as antitumor agents" (WO 2010061208 A2), "Preparation of 4-aminoquinazoline derivatives as antineoplastic agents (CN 101367793 A)", "Preparation of proline quinazoline derivatives as antiproliferative agents (BR 2006002275 A)", "Preparation of quinazoline derivatives as protein kinase inhibitors" (WO 2005097137 A2), "Preparation of quinazoline derivatives as protein kinase inhibitors" (WO 2005097134 A2), "Preparation of quinazoline derivatives as EGFR tyrosine kinase inhibitors" (WO 2005028469 A1), "Preparation of phenylamino-substituted quinazolines as inhibitors of EGF and ErbB-2 kinases" (WO 2005028470 A1), "Preparation of quinazoline derivatives as EGFR tyrosine kinase inhibitors" (WO 2005026156 A1), "Preparation of piperidyl-quinazoline derivatives as tyrosine kinase inhibitors for the treatment of tumors" (WO 2005012290 A1), "Preparation of 4-anilinoquinazolines as antiproliferative agents" (WO 2003082831 A1), "Preparation of aminoquinazolines as epidermal growth factor receptor signal transduction inhibitors" (WO 2002018351 A1), "Preparation of quinazolines as aurora 2 kinase inhibitors" (WO 2001021594 A1), "Quinazolines and other bicyclic heterocycles, pharmaceutical compositions containing these compounds as tyrosine kinase inhibitors, and processes for preparing them" (WO 2000055141 A1), "Preparation of quinazoline derivatives and their receptor tyrosine kinase inhibitory properties" (WO 9738994 A1), "Quinazoline derivatives as antitumor agents" (WO 9730034 A1), "Preparation of haloanilinoquinazolines as Class I receptor tyrosine kinase inhibitors" (WO 9633980 A1) and "Quinazoline derivatives useful for treatment of neoplastic disease" (U.S. Pat. No. 5,457,105).

The compounds of the invention, or a pharmaceutically acceptable salt thereof, when compared with other clinically available EGFR inhibitors, exhibit certain improved properties e.g. higher BBB penetration (thus making them potentially useful for the treatment of cancers that have metastasised to the CNS, in particular brain metastases and leptomeningeal metastases); show better selectivity between WT EGFR and mutant EGFR (which may result in less treatment side effects of skin rash and diarrhoea); whilst maintaining equivalent or improved activity against activating mutant EGFR (e.g. EGFR L858R activating mutant and/or the Exon 19 deletion activating mutants). Therefore, such compounds, or a pharmaceutically acceptable salt thereof, may be especially useful in the treatment of disease states in which these activating mutations of EGFR are implicated, for example in the treatment of cancer.

Accordingly, the present invention provides a compound of formula (I):

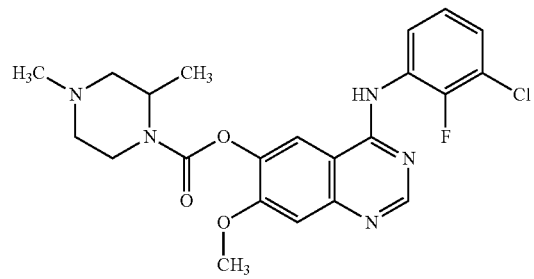

(I)

or a pharmaceutically acceptable salt thereof.

The structures of the clinical compounds referred to above are as follows:

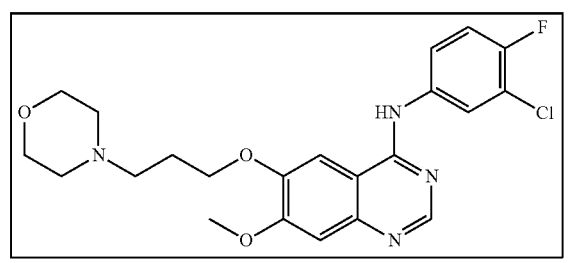

gefitinib

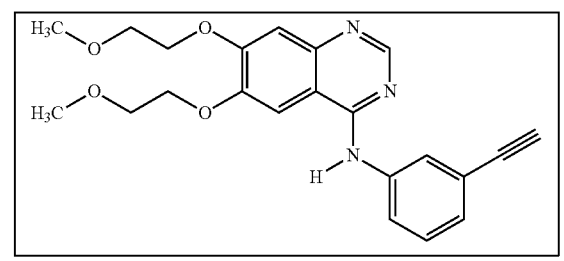

erlotinib

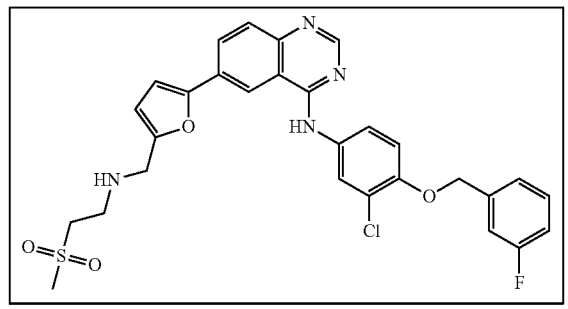

lapatinib

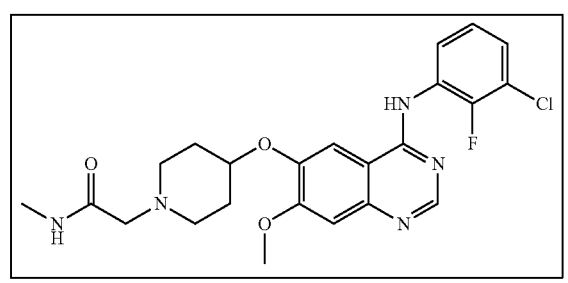

sapitinib

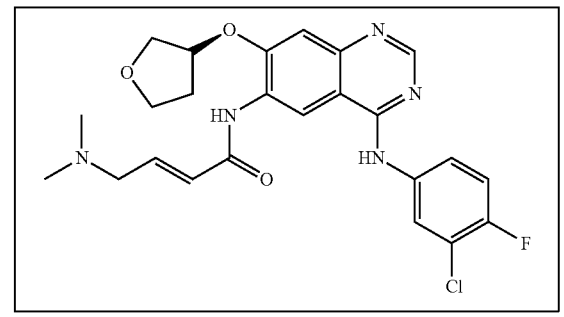

afatinib

-continued

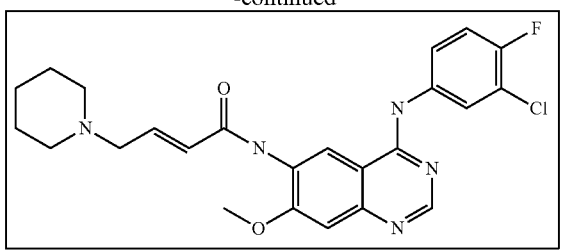

dacomitinib

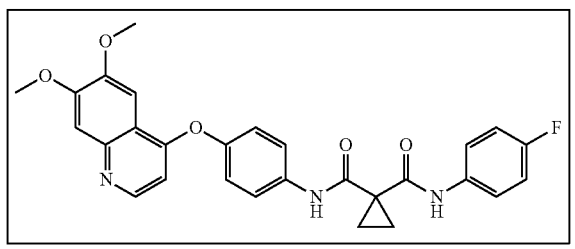

cabozantinib

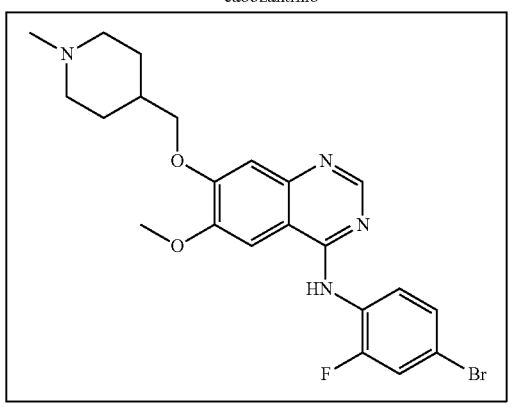

vandetanib

A suitable pharmaceutically acceptable salt of a compound of the invention is, for example, an acid-addition salt, for example an inorganic or organic acid, for example hydrochloric, hydrobromic, sulphuric, phosphoric, citric, L-tartaric, glycolic, fumaric, succinic or maleic acid, especially hydrochloric, hydrobromic, sulphuric, phosphoric, citric, L-tartaric, glycolic, fumaric or maleic acid. A particular pharmaceutically acceptable salt of a compound of the invention is a hydrochloric acid salt. A further particular pharmaceutically acceptable salt of a compound of the invention is a succinic acid salt.

Salts of the compounds of formula (I) may be formed, for example, by reacting the compound of formula (I) with an amount of acid in a medium such as one in which the salt precipitates or in an aqueous medium followed by lyophilization.

The compounds of formula (I), or a pharmaceutically acceptable salt thereof, have a chiral centre. It is to be understood that the invention encompasses all stereoisomers (enantiomers and diastereoisomers) of the compounds of formula (I), or a pharmaceutically acceptable salt thereof, which possess activating mutant EGFR inhibitory activity. The invention further relates to any and all tautomeric forms of the compounds of formula (I), or a pharmaceutically acceptable salt thereof, that possess activating mutant EGFR inhibitory activity. In a further aspect of the invention there is provided an enantiomer of formula (I), or a pharmaceutically acceptable salt thereof, substantially free of any other enantiomers. In a further aspect of the invention there is provided the (R)-enantiomer of formula (I), or a pharmaceutically acceptable salt thereof, substantially free of any other enantiomers. In a further aspect of the invention there is provided the (S)-enantiomer of formula (I), or a pharmaceutically acceptable salt thereof, substantially free of any other enantiomers.

In one embodiment of the invention where the mixture comprises unequal molar proportions of enantiomers, the mixture may have an enantiomeric excess selected from >50%, >70%, >90% and >95%. Particularly the mixture may have an enantiomeric excess >98%. More particularly the mixture may have an enantiomeric excess >99%. More particularly the mixture may have an enantiomeric excess >99.5%.

It is also to be understood that certain compounds of formula (I), or a pharmaceutically acceptable salt thereof, can exist in solvated as well as unsolvated forms such as, for example, hydrated forms. It is to be understood that the invention encompasses all such solvated forms which possess activating mutant EGFR inhibitory activity.

It is further to be understood that the invention encompasses all isotopic forms of the compounds described herein. For example hydrogen includes deuterium and carbon includes $^{12}C$ and $^{13}C$.

In another aspect of the invention, particular compounds of the invention are any one of the Examples or a pharmaceutically acceptable salt thereof In another aspect of the invention, particular compounds of the invention are selected from:
4-[(3-chloro-2-fluorophenyl)amino]-7-methoxyquinazolin-6-yl (2R)-2,4-dimethylpiperazine-1-carboxylate;
4-[(3-chloro-2-fluorophenyl)amino]-7-methoxyquinazolin-6-yl (2S)-2,4-dimethylpiperazine-1-carboxylate; and
4-[(3-chloro-2-fluorophenyl)amino]-7-methoxyquinazolin-6-yl (±) 2,4-dimethylpiperazine-1-carboxylate;
or a pharmaceutically acceptable salt thereof.

In another aspect of the invention, particular compounds of the invention are selected from:
4-[(3-chloro-2-fluorophenyl)amino]-7-methoxyquinazolin-6-yl (2R)-2,4-dimethylpiperazine-1-carboxylate;
4-[(3-chloro-2-fluorophenyl)amino]-7-methoxyquinazolin-6-yl (2S)-2,4-dimethylpiperazine-1-carboxylate; and
4-[(3-chloro-2-fluorophenyl)amino]-7-methoxyquinazolin-6-yl (±) 2,4-dimethylpiperazine-1-carboxylate.

In another aspect of the invention, a particular compound of the invention is selected from a pharmaceutically acceptable salt of 4-[(3-chloro-2-fluorophenyl)amino]-7-methoxyquinazolin-6-yl (2R)-2,4-dimethylpiperazine-1-carboxylate.

In another aspect of the invention, a particular compound of the invention is selected from 4-[(3-chloro-2-fluorophenyl)amino]-7-methoxyquinazolin-6-yl (2R)-2,4-dimethylpiperazine-1-carboxylate hydrochloride.

In another aspect of the invention, a particular compound of the invention is selected from 4-[(3-chloro-2-fluorophenyl)amino]-7-methoxyquinazolin-6-yl (2R)-2,4-dimethylpiperazine-1-carboxylate succinate.

In another aspect of the invention, a particular compound of the invention is selected from 4-[(3-chloro-2-fluorophenyl)amino]-7-methoxyquinazolin-6-yl (2R)-2,4-dimethylpiperazine-1-carboxylate.

In another aspect of the invention, a particular compound of the invention is selected from a pharmaceutically acceptable salt of 4-[(3-chloro-2-fluorophenyl)amino]-7-methoxyquinazolin-6-yl (2S)-2,4-dimethylpiperazine-1-carboxylate.

In another aspect of the invention, a particular compound of the invention is selected from 4-[(3-chloro-2-fluorophenyl)amino]-7-methoxyquinazolin-6-yl (2S)-2,4-dimethylpiperazine-1-carboxylate.

In another aspect of the invention, a particular compound of the invention is selected from a pharmaceutically acceptable salt of 4-[(3-chloro-2-fluorophenyl)amino]-7-methoxyquinazolin-6-yl (−)-2,4-dimethylpiperazine-1-carboxylate.

In another aspect of the invention, a particular compound of the invention is selected from 4-[(3-chloro-2-fluorophenyl)amino]-7-methoxyquinazolin-6-yl (−)-2,4-dimethylpiperazine-1-carboxylate.

In another aspect of the invention, a particular compound of the invention is selected from a pharmaceutically acceptable salt of 4-[(3-chloro-2-fluorophenyl)amino]-7-methoxyquinazolin-6-yl (+)-2,4-dimethylpiperazine-1-carboxylate.

In another aspect of the invention, a particular compound of the invention is selected from 4-[(3-chloro-2-fluorophenyl)amino]-7-methoxyquinazolin-6-yl (+)-2,4-dimethylpiperazine-1-carboxylate.

In another aspect of the invention, a particular compound of the invention is selected from a pharmaceutically acceptable salt of 4-[(3-chloro-2-fluorophenyl)amino]-7-methoxyquinazolin-6-yl (±) 2,4-dimethylpiperazine-1-carboxylate.

In another aspect of the invention, a particular compound of the invention is selected from 4-[(3-chloro-2-fluorophenyl)amino]-7-methoxyquinazolin-6-yl (±) 2,4-dimethylpiperazine-1-carboxylate.

Herein where optical rotations of (+) or (−) are quoted, particularly they are measured at a c10 where c is the concentration in g/mL, in DMSO at 25° C.

It is also to be understood that certain compounds of the invention, or a pharmaceutically acceptable salt thereof, may exist in certain crystalline forms. In particular 4-[(3-chloro-2-fluorophenyl)amino]-7-methoxyquinazolin-6-yl (2R)-2,4-dimethylpiperazine-1-carboxylate, has been identified as having several crystalline forms—particularly Form A, Form E, Form I and Form J. In addition the hydrochloride salt of 4-[(3-chloro-2-fluorophenyl)amino]-7-methoxyquinazolin-6-yl (2R)-2,4-dimethylpiperazine-1-carboxylate may also exist in crystalline form—particularly mono-HCl salt Form $A_1$ and succinate salt Form $A_S$. It is to be understood that the present invention encompasses all such crystalline forms of the compounds of formula (I), or a pharmaceutically acceptable salt thereof, which possess activating mutant EGFR inhibitory activity.

Figure 1:
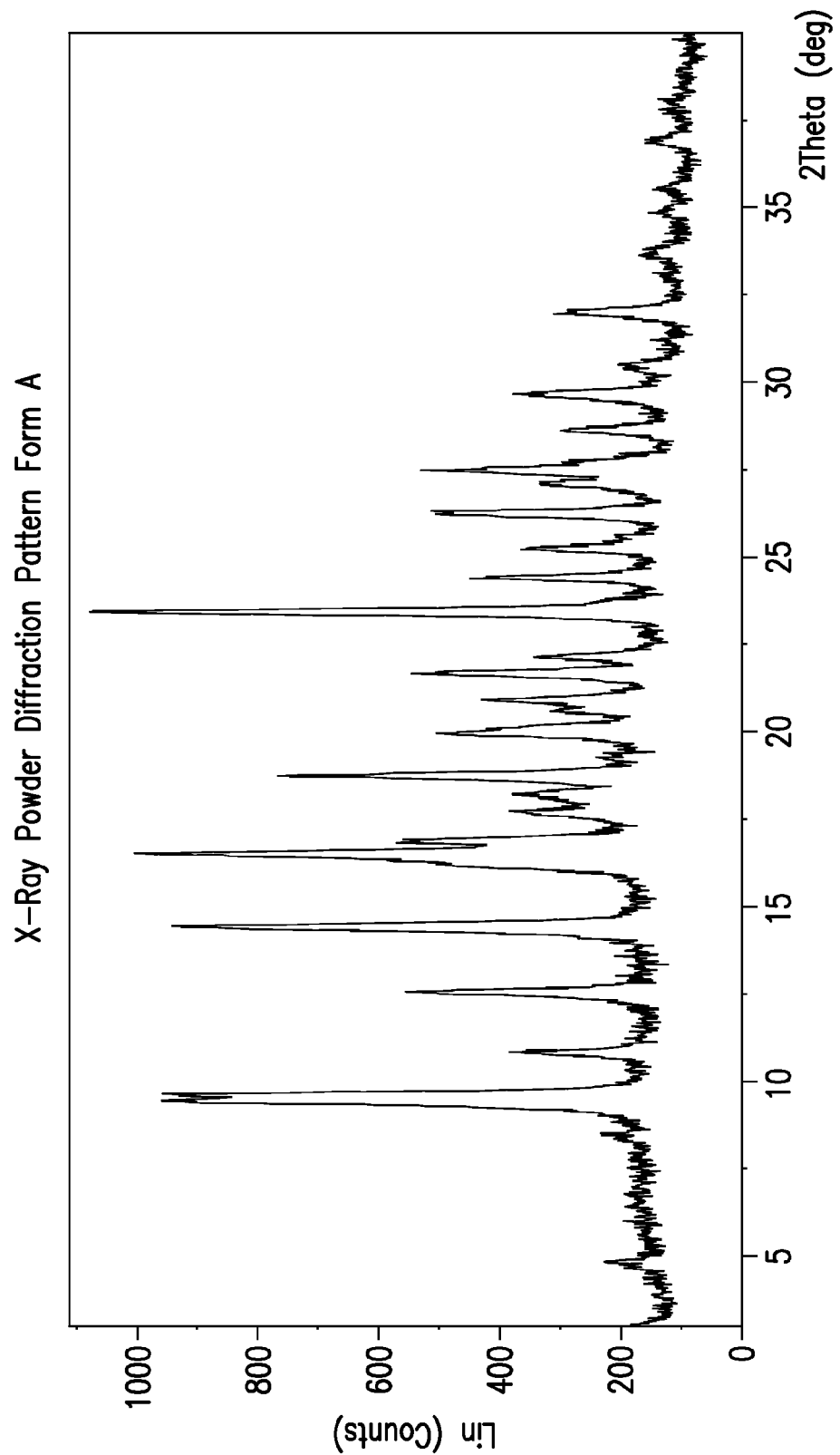

4-[(3-Chloro-2-fluorophenyl)amino]-7-methoxyquinazolin-6-yl (2R)-2,4-dimethylpiperazine-1-carboxylate in crystalline form, Form A Form A is characterised in providing at least one of the following 2θ values measured using CuKa radiation: 23.3 and 14.3°. Form A is characterised in providing an X-ray powder diffraction pattern, substantially as shown in FIG. 1. Ten X-Ray powder diffraction peaks are shown in Table A:

TABLE A

| Ten X-Ray Powder Diffraction peaks for Form A | |
| --- | --- |
| Angle 2-Theta (2θ) | Intensity % |
| 23.3 | 100.00 |
| 14.3 | 83.70 |
| 9.4 | 78.08 |
| 18.6 | 61.70 |
| 16.3 | 60.41 |

TABLE A-continued

| Ten X-Ray Powder Diffraction peaks for Form A | |
| --- | --- |
| Angle 2-Theta (2θ) | Intensity % |
| 21.5 | 39.61 |
| 12.4 | 38.89 |
| 26.1 | 38.18 |
| 19.8 | 35.71 |
| 27.4 | 31.12 |

According to the present invention there is provided a crystalline form, Form A, which has an X-ray powder diffraction pattern with at least two specific peaks at about 2-theta=23.3° and 14.3°.

According to the present invention there is provided a crystalline form, Form A, which has an X-ray powder diffraction pattern with specific peaks at about 2-theta=23.3, 14.3, 9.4, 18.6, 16.3, 21.5, 12.4, 26.1, 19.8, 27.4°.

According to the present invention there is provided crystalline form, Form A which has an X-ray powder diffraction pattern substantially the same as the X-ray powder diffraction pattern shown in FIG. 1.

According to the present invention there is provided a crystalline form, Form A, which has an X-ray powder diffraction pattern with at least two specific peaks at 2-theta=23.3° and 14.3° wherein said values may be plus or minus 0.2° 2-theta.

According to the present invention there is provided a crystalline form, Form A, which has an X-ray powder diffraction pattern with specific peaks at 2-theta=23.3, 14.3, 9.4, 18.6, 16.3, 21.5, 12.4, 26.1, 19.8, 27.4° wherein said values may be plus or minus 0.2° 2-theta.

DSC analysis of Form A shows a melting endotherm with an onset of 192.4° C. and a peak at 195.8° C. (FIG. 2).

Figure 3:
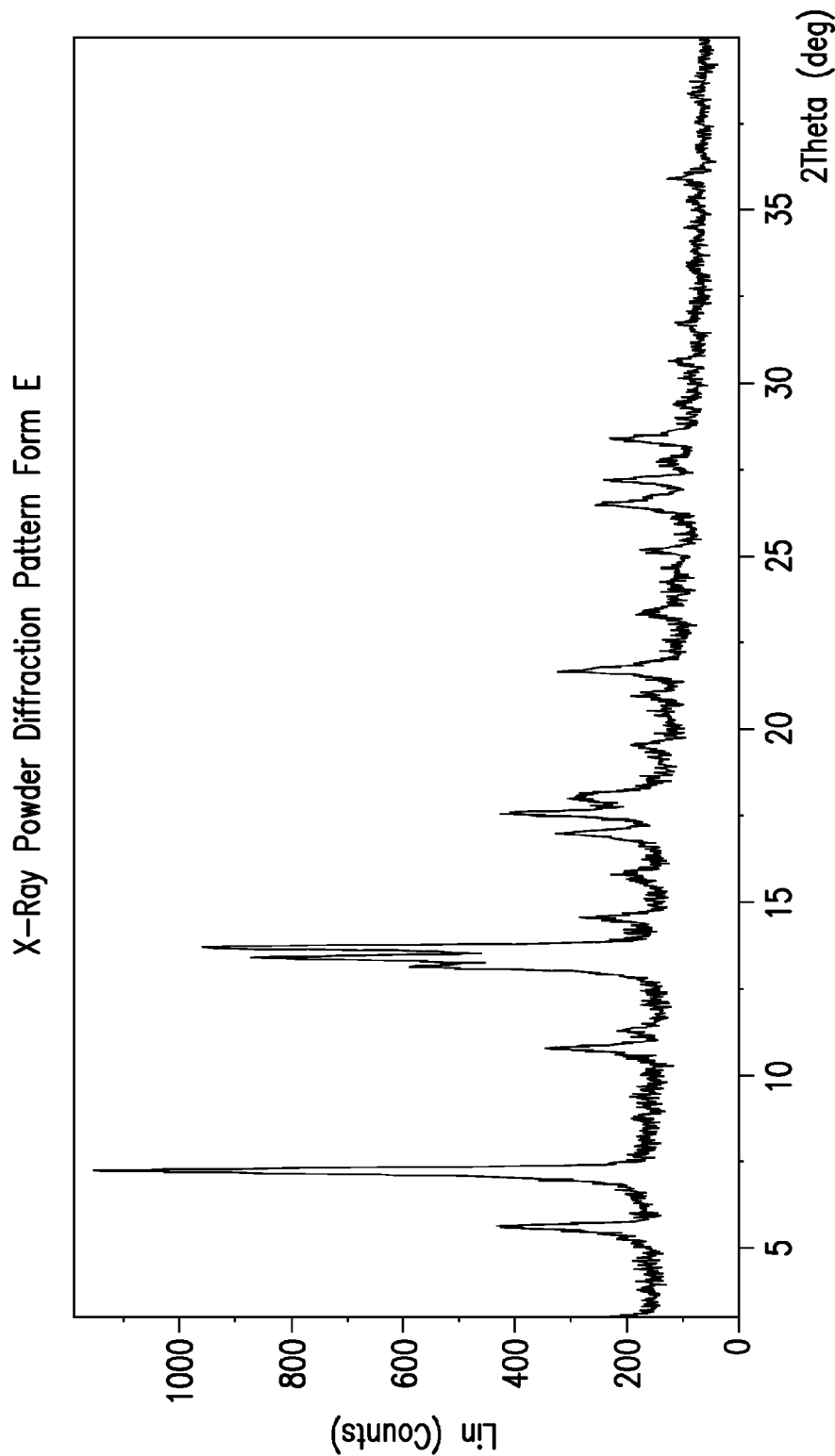

4-[(3-Chloro-2-fluorophenyl)amino]-7-methoxyquinazolin-6-yl (2R)-2,4-dimethylpiperazine-1-carboxylate in crystalline form, Form E Form E is characterised in providing at least one of the following 2θ values measured using CuKa radiation: 7.3 and 13.7°. Form E is characterised in providing an X-ray powder diffraction pattern, substantially as shown in FIG. 3. Nine X-Ray powder diffraction peaks are shown in Table B:

TABLE B

| Nine X-Ray Powder Diffraction peaks for Form E | |
| --- | --- |
| Angle 2-Theta (2θ) | Intensity % |
| 7.3 | 100.00 |
| 13.7 | 81.83 |
| 13.4 | 74.07 |
| 17.6 | 28.89 |
| 5.6 | 28.02 |
| 10.8 | 19.08 |
| 21.7 | 19.04 |
| 26.5 | 17.10 |
| 28.4 | 13.41 |

According to the present invention there is provided a crystalline form, Form E, which has an X-ray powder diffraction pattern with at least two specific peaks at about 2-theta=7.3° and 13.7°.

According to the present invention there is provided a crystalline form, Form E, which has an X-ray powder diffraction pattern with specific peaks at about 2-theta=7.3, 13.7, 13.4, 17.6, 5.6, 10.8, 21.7, 26.5, 28.4°.

According to the present invention there is provided crystalline form, Form E which has an X-ray powder diffraction pattern substantially the same as the X-ray powder diffraction pattern shown in FIG. 3.

According to the present invention there is provided a crystalline form, Form E, which has an X-ray powder diffraction pattern with at least two specific peaks at 2-theta=7.3° and 13.7° wherein said values may be plus or minus 0.2° 2-theta.

According to the present invention there is provided a crystalline form, Form E, which has an X-ray powder diffraction pattern with specific peaks at 2-theta=7.3, 13.7, 13.4, 17.6, 5.6, 10.8, 21.7, 26.5, 28.4° wherein said values may be plus or minus 0.2° 2-theta.

DSC analysis of Form E shows a melting endotherm with an onset of 194.2° C. and a peak at 196.3° C. (FIG. 4).

Figure 5:
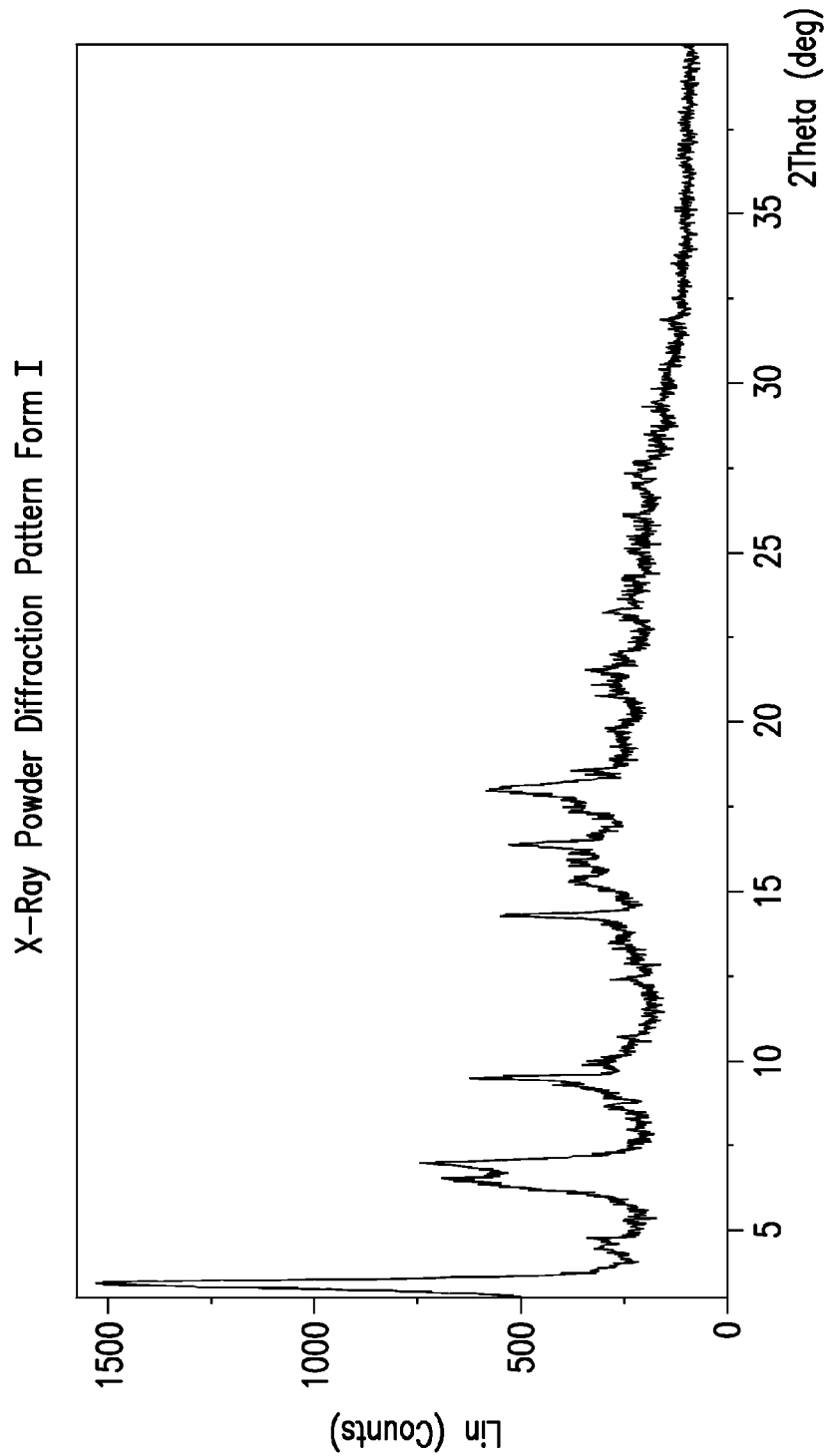

4-[(3-Chloro-2-fluorophenyl)amino]-7-methoxyquinazolin-6-yl (2R)-2,4-dimethylpiperazine-1-carboxylate in crystalline form, Form I Form I is characterised in providing at least one of the following 2θ values measured using CuKa radiation: 3.5 and 7.0°. Form I is characterised in providing an X-ray powder diffraction pattern, substantially as shown in FIG. 5. Ten X-Ray powder diffraction peaks are shown in Table C:

TABLE C

Ten X-Ray Powder Diffraction peaks for Form I

| Angle 2-Theta (2θ) | Intensity % |
|---|---|
| 3.5 | 100.00 |
| 7.0 | 41.22 |
| 9.5 | 32.57 |
| 6.4 | 32.54 |
| 14.3 | 25.70 |
| 18.0 | 24.80 |
| 16.4 | 22.12 |
| 15.3 | 10.95 |
| 4.7 | 7.05 |
| 21.3 | 4.54 |

According to the present invention there is provided a crystalline form, Form I, which has an X-ray powder diffraction pattern with at least three specific peaks at about 2-theta 3.5°, 7.0° and 9.5°.

According to the present invention there is provided a crystalline form, Form I, which has an X-ray powder diffraction pattern with specific peaks at about 2-theta=3.5, 7.0, 9.5, 6.4, 14.3, 18.0, 16.4, 15.3, 4.7, 21.3°.

According to the present invention there is provided crystalline form, Form I which has a X-ray powder diffraction pattern substantially the same as the X-ray powder diffraction pattern shown in FIG. 5.

According to the present invention there is provided a crystalline form, Form I, which has an X-ray powder diffraction pattern with at least three specific peaks at 2-theta=3.5°, 7.0° and 9.5° wherein said values may be plus or minus 0.2° 2-theta.

According to the present invention there is provided a crystalline form, Form I, which has an X-ray powder diffraction pattern with specific peaks at 2-theta=3.5, 7.0, 9.5, 6.4, 14.3, 18.0, 16.4, 15.3, 4.7, 21.3° wherein said values may be plus or minus 0.2° 2-theta.

DSC analysis of Form I shows a melting endotherm with an onset of 193.3° C. and a peak at 195.9° C. (FIG. 6).

Figure 7:
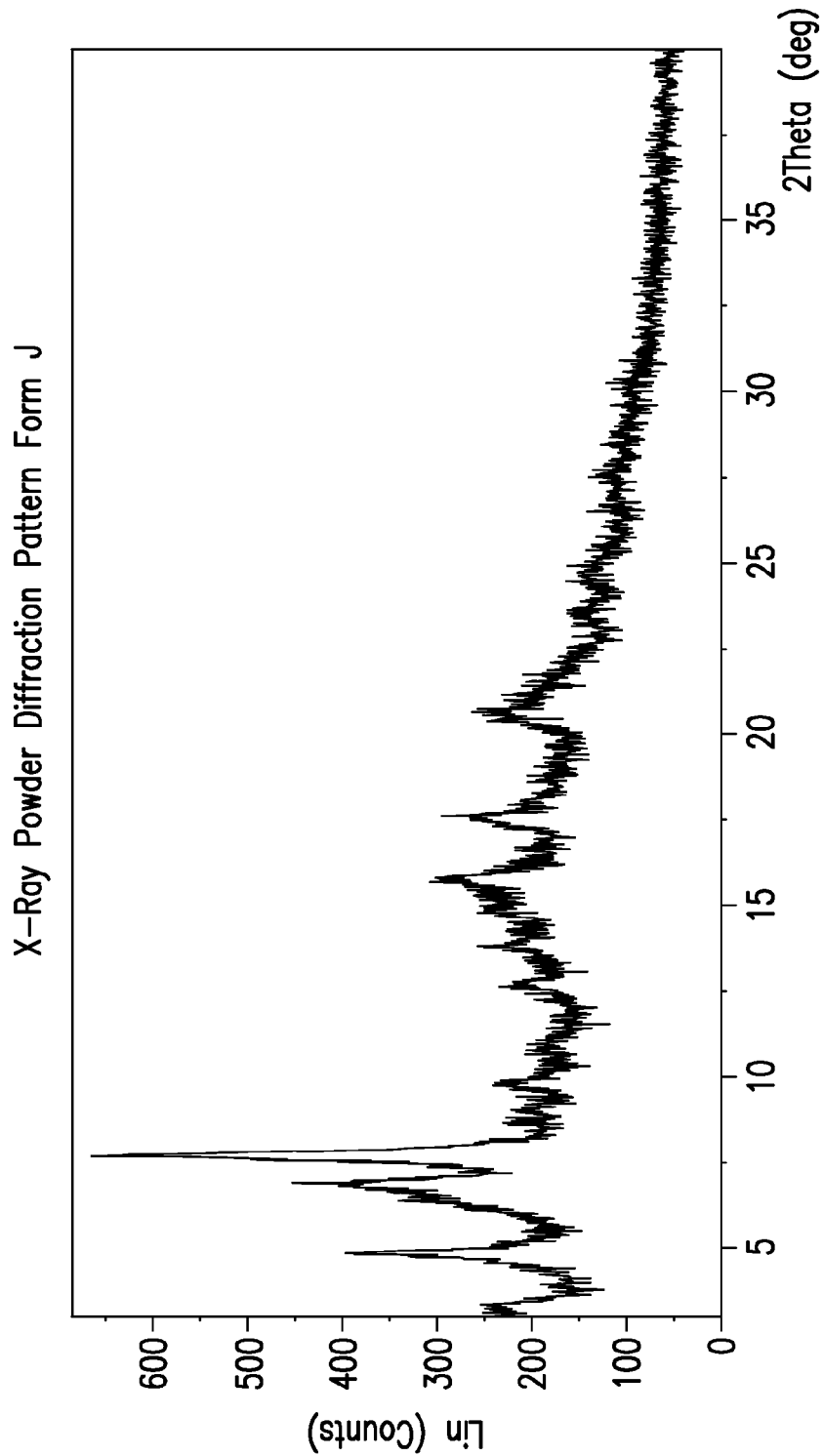

4-[(3-Chloro-2-fluorophenyl)amino]-7-methoxyquinazolin-6-yl (2R)-2,4-dimethylpiperazine-1-carboxylate in crystalline form, Form J Form J is characterised in providing at least one of the following 2θ values measured using CuKa radiation: 7.8 and 7.0°. Form J is characterised in providing an X-ray powder diffraction pattern, substantially as shown in FIG. 7. Ten X-Ray powder diffraction peaks are shown in Table D:

TABLE D

Ten X-Ray Powder Diffraction peaks for Form J

| Angle 2-Theta (2θ) | Intensity % |
|---|---|
| 7.8 | 100.00 |
| 7.0 | 49.36 |
| 4.9 | 45.57 |
| 15.9 | 27.11 |
| 17.7 | 20.89 |
| 3.4 | 17.30 |
| 20.7 | 16.71 |
| 9.8 | 14.59 |
| 13.9 | 14.11 |
| 12.7 | 10.83 |

According to the present invention there is provided a crystalline form, Form J, which has an X-ray powder diffraction pattern with at least two specific peaks at about 2-theta=7.8° and 7.0°.

According to the present invention there is provided a crystalline form, Form J, which has an X-ray powder diffraction pattern with specific peaks at about 2-theta=7.8, 7.0, 4.9, 15.9, 17.7, 3.4, 20.7, 9.8, 13.9, 12.7 °.

According to the present invention there is provided crystalline form, Form J which has an X-ray powder diffraction pattern substantially the same as the X-ray powder diffraction pattern shown in FIG. 7.

According to the present invention there is provided a crystalline form, Form J, which has an X-ray powder diffraction pattern with at least two specific peaks at 2-theta=7.8° and 7.0° wherein said values may be plus or minus 0.2° 2-theta.

According to the present invention there is provided a crystalline form, Form J, which has an X-ray powder diffraction pattern with specific peaks at 2-theta=7.8, 7.0, 4.9, 15.9, 17.7, 3.4, 20.7, 9.8, 13.9, 12.7° wherein said values may be plus or minus 0.2° 2-theta.

DSC analysis of Form J shows a melting endotherm with an onset of 193.3° C. and a peak at 195.8° C. (FIG. 8).

Figure 9:
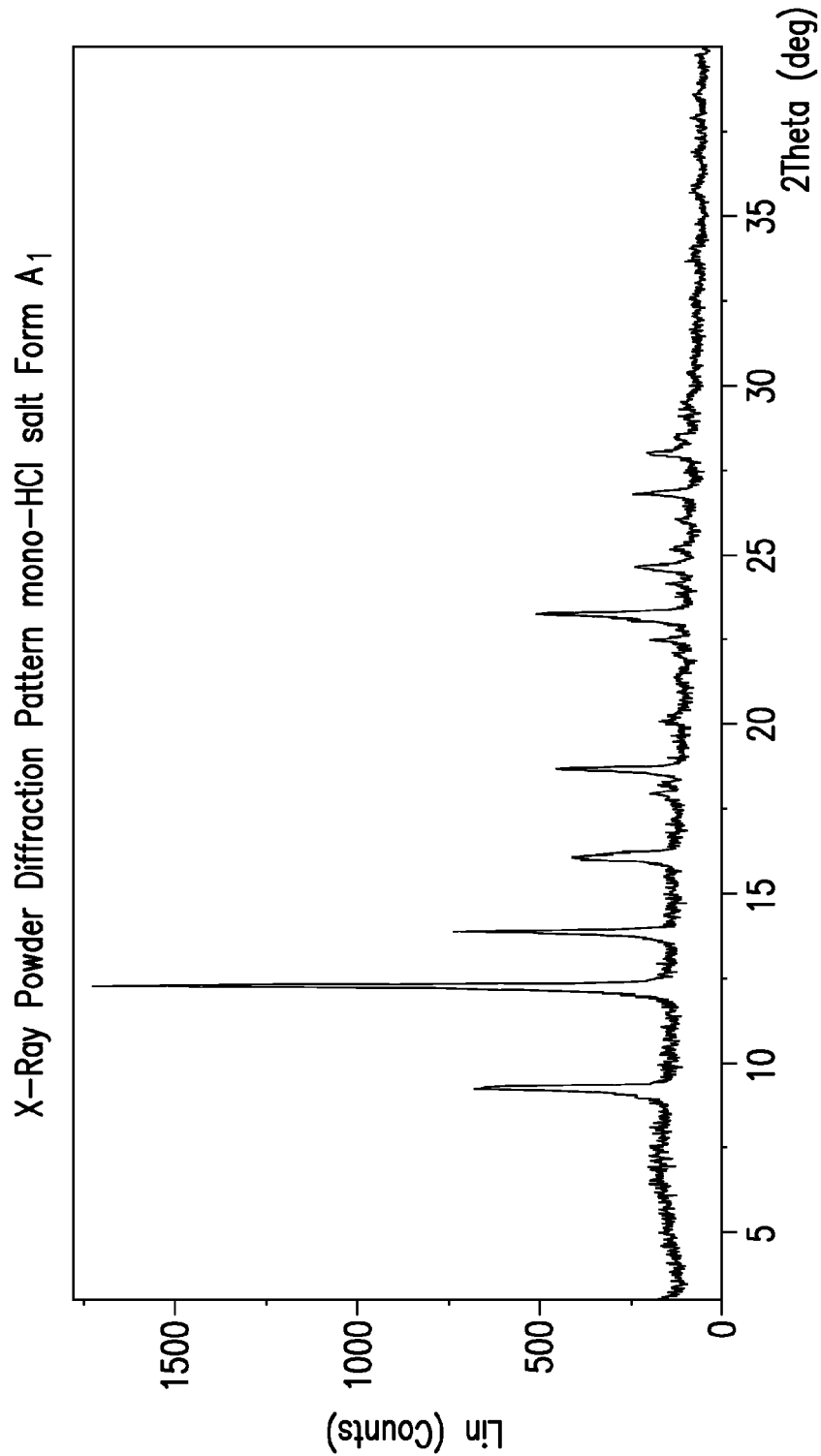

4-[(3-Chloro-2-fluorophenyl)amino]-7-methoxyquinazolin-6-yl (2R)-2,4-dimethylpiperazine-1-carboxylate hydrochloride salt in crystalline form, mono-HCl salt Form $A_1$ Mono-HCl salt Form $A_1$ is characterised in providing at least one of the following 2θ values measured using CuKa radiation: 12.3 and 13.9°. Mono-HCl salt Form $A_1$ is characterised in providing an X-ray powder diffraction pattern, substantially as shown in FIG. 9. Nine X-Ray powder diffraction peaks are shown in Table E:

TABLE E

Nine X-Ray Powder Diffraction peaks for mono-HCl salt Form A₁

| Angle 2-Theta (2θ) | Intensity % |
|---|---|
| 12.3 | 100.00 |
| 13.9 | 40.45 |
| 9.3 | 29.34 |
| 23.3 | 26.42 |
| 18.7 | 20.54 |
| 16.0 | 17.94 |
| 24.6 | 10.24 |
| 26.8 | 8.94 |
| 28.0 | 7.90 |

According to the present invention there is provided a crystalline form, mono-HCl salt Form $A_1$ which has an X-ray powder diffraction pattern with at least two specific peaks at about 2-theta=12.3° and 13.9°.

According to the present invention there is provided a crystalline form, mono-HCl salt Form $A_1$ which has an X-ray powder diffraction pattern with specific peaks at about 2-theta=12.3, 13.9, 9.3, 23.3, 18.7, 16.0, 24.6, 26.8, 28.0°.

According to the present invention there is provided crystalline form, mono-HCl salt Form $A_1$ which has an X-ray powder diffraction pattern substantially the same as the X-ray powder diffraction pattern shown in FIG. 9.

According to the present invention there is provided a crystalline form, mono-HCl salt Form $A_1$ which has an X-ray powder diffraction pattern with at least two specific peaks at 2-theta=12.3° and 13.9° wherein said values may be plus or minus 0.2° 2-theta.

According to the present invention there is provided a crystalline form, mono-HCl salt Form $A_1$ which has an X-ray powder diffraction pattern with specific peaks at 2-theta=12.3, 13.9, 9.3, 23.3, 18.7, 16.0, 24.6, 26.8, 28.0° wherein said values may be plus or minus 0.2° 2-theta.

DSC analysis of mono-HCl salt Form $A_1$ shows a melting endotherm with an onset of 259.6° C. and a peak at 261.4° C. (FIG. 10).

4-[(3-Chloro-2-fluorophenyl)amino]-7-methoxyquinazolin-6-yl (2R)-2,4-dimethylpiperazine-1-carboxylate succinate salt in crystalline form, succinate salt Form $A_8$ Succinate salt Form $A_8$ is characterised in providing at least one of the following 2θ values measured using CuKa radiation: 6.5 and 17.7. Succinate salt Form $A_8$ is characterised in providing an X-ray powder diffraction pattern, substantially as shown in FIG. 11. Nine X-Ray powder diffraction peaks are shown in Table F:

TABLE F

| Angle 2-Theta (2θ) | Intensity % |
|---|---|
| 6.5 | 100.00 |
| 17.7 | 31.30 |
| 14.7 | 24.91 |
| 9.2 | 21.73 |
| 26.5 | 14.13 |
| 20.2 | 12.03 |
| 13.1 | 11.74 |
| 27.3 | 9.72 |
| 24.0 | 5.56 |

According to the present invention there is provided a crystalline form, Succinate salt Form $A_8$ which has an X-ray powder diffraction pattern with at least three specific peaks at about 2-theta=6.5°, 17.7° and 14.7°.

According to the present invention there is provided a crystalline form, Succinate salt Form $A_8$ which has an X-ray powder diffraction pattern with specific peaks at about 2-theta=6.5, 17.7, 14.7, 9.2, 26.5, 20.2, 13.1, 27.3, 24.0°.

According to the present invention there is provided crystalline form, Succinate salt Form $A_8$ which has an X-ray powder diffraction pattern substantially the same as the X-ray powder diffraction pattern shown in FIG. 11.

According to the present invention there is provided a crystalline form, Succinate salt Form $A_8$ which has an X-ray powder diffraction pattern with at least three specific peaks at 2-theta=6.5°, 17.7° and 14.7° wherein said values may be plus or minus 0.2° 2-theta.

According to the present invention there is provided a crystalline form, Succinate salt Form $A_8$ which has an X-ray powder diffraction pattern with specific peaks at 2-theta=6.5, 17.7, 14.7, 9.2, 26.5, 20.2, 13.1, 27.3, 24.0° wherein said values may be plus or minus 0.2° 2-theta.

DSC analysis shows Succinate salt Form $A_8$ shows a melting endotherm with an onset of 191.8° C. and a peak at 194.2° C. (FIG. 12).

LEGENDS TO FIGURES

FIG. 1: X-Ray Powder Diffraction Pattern of Form A
FIG. 2: DSC Thermogram of Form A
FIG. 3: X-Ray Powder Diffraction Pattern of Form E
FIG. 4: DSC Thermogram of Form E
FIG. 5: X-Ray Powder Diffraction Pattern of Form I
FIG. 6: DSC Thermogram of Form I
FIG. 7: X-Ray Powder Diffraction Pattern of Form J
FIG. 8: DSC Thermogram of Form J
FIG. 9: X-Ray Powder Diffraction Pattern of mono-HCl salt Form $A_1$
FIG. 10: DSC Thermogram of mono-HCl salt Form $A_1$
FIG. 11: X-Ray Powder Diffraction Pattern of Succinate salt Form $A_8$
FIG. 12: DSC Thermogram of Succinate salt Form $A_8$ When it is stated that the present invention relates to a crystalline form, the degree of crystallinity is conveniently greater than about 60%, more conveniently greater than about 80%, conveniently greater than about 90% and more conveniently greater than about 95%. Most conveniently the degree of crystallinity is greater than about 98%.

It will be understood that the 2-theta values of the X-ray powder diffraction pattern may vary slightly from one machine to another or from one sample to another, and so the values quoted are not to be construed as absolute. It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the polymorphic forms of the present invention are not limited to the crystals that provide X-ray powder diffraction patterns identical to the X-ray powder diffraction pattern shown in the figures, and any crystals providing X-ray powder diffraction patterns substantially the same as those shown in the figures fall within the scope of the present invention. A person skilled in the art of X-ray powder diffraction is able to judge the substantial identity of X-ray powder diffraction patterns.

Persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.2° 2-theta, and such degree of a measurement error should be taken into account when considering the X-ray powder diffraction patterns shown in the figures and tables. Furthermore, it should be understood that intensities might fluctuate depending on experimental conditions and sample preparation (preferred orientation).

Therefore, in a further aspect of the invention there is provided 4-[(3-chloro-2-fluorophenyl)amino]-7-methoxyquinazolin-6-yl (2R)-2,4-dimethylpiperazine-1-carboxylate in crystalline form.

In a further aspect of the invention there is provided a pharmaceutically acceptable salt of 4-[(3-chloro-2-fluorophenyl)amino]-7-methoxyquinazolin-6-yl (2R)-2,4-dimethylpiperazine-1-carboxylate in crystalline form.

In a further aspect of the invention there is provided a hydrochloride salt of 4-[(3-chloro-2-fluorophenyl)amino]-7-methoxyquinazolin-6-yl (2R)-2,4-dimethylpiperazine-1-carboxylate in crystalline form.

In one aspect of the invention, 4-[(3-chloro-2-fluorophenyl)amino]-7-methoxyquinazolin-6-yl (2R)-2,4-dimethylpiperazine-1-carboxylate in crystalline form is in the form of Form A.

In one aspect of the invention, 4-[(3-chloro-2-fluorophenyl)amino]-7-methoxyquinazolin-6-yl (2R)-2,4-dimethylpiperazine-1-carboxylate in crystalline form is in the form of Form E.

In one aspect of the invention, 4-[(3-chloro-2-fluorophenyl)amino]-7-methoxyquinazolin-6-yl (2R)-2,4-dimethylpiperazine-1-carboxylate in crystalline form is in the form of Form I.

In one aspect of the invention, 4-[(3-chloro-2-fluorophenyl)amino]-7-methoxyquinazolin-6-yl (2R)-2,4-dimethylpiperazine-1-carboxylate in crystalline form is in the form of Form J.

In one aspect of the invention, the hydrochloride salt of 4-[(3-chloro-2-fluorophenyl)amino]-7-methoxyquinazolin-6-yl (2R)-2,4-dimethylpiperazine-1-carboxylate in crystalline form is in the form of mono-HCl salt Form $A_1$.

In one aspect of the invention, the succinate salt of 4-[(3-chloro-2-fluorophenyl)amino]-7-methoxyquinazolin-6-yl (2R)-2,4-dimethylpiperazine-1-carboxylate in crystalline form is in the form of succinate salt Form $A_8$.

In one aspect of the invention, 4-[(3-chloro-2-fluorophenyl)amino]-7-methoxyquinazolin-6-yl (2R)-2,4-dimethylpiperazine-1-carboxylate in crystalline form is in the form of Form A and is substantially free of any other Forms.

In one aspect of the invention, 4-[(3-chloro-2-fluorophenyl)amino]-7-methoxyquinazolin-6-yl (2R)-2,4-dimethylpiperazine-1-carboxylate in crystalline form is in the form of Form E and is substantially free of any other Forms.

In one aspect of the invention, 4-[(3-chloro-2-fluorophenyl)amino]-7-methoxyquinazolin-6-yl (2R)-2,4-dimethylpiperazine-1-carboxylate in crystalline form is in the form of Form I and is substantially free of any other Forms.

In one aspect of the invention, 4-[(3-chloro-2-fluorophenyl)amino]-7-methoxyquinazolin-6-yl (2R)-2,4-dimethylpiperazine-1-carboxylate in crystalline form is in the form of Form J and is substantially free of any other Forms.

In one aspect of the invention the hydrochloride salt of 4-[(3-chloro-2-fluorophenyl)amino]-7-methoxyquinazolin-6-yl (2R)-2,4-dimethylpiperazine-1-carboxylate in crystalline form is in the form of mono-HCl salt Form $A_1$ and is substantially free of any other Forms.

In one aspect of the invention the succinate salt of 4-[(3-chloro-2-fluorophenyl)amino]-7-methoxyquinazolin-6-yl (2R)-2,4-dimethylpiperazine-1-carboxylate in crystalline form is in the form of Succinate salt Form $A_8$ and is substantially free of any other Forms.

The term "substantially free" refers to less than 10% of another Form or Forms, enantiomer or enantiomers, particularly less than 5%. In another aspect "substantially free" refers to less than 1% of another Form or Forms, enantiomer or enantiomers As stated hereinbefore the compounds, or a pharmaceutically acceptable salt thereof, defined in the present invention possess anti-cancer activity which is believed to arise from the activating mutant EGFR inhibitory activity, and other properties, of the compounds, or a pharmaceutically acceptable salt thereof. These properties may be assessed, for example, using the procedures set out below.

Assay 1: Cellular Phosphorylation Assay

The human lung cell line NCI-H3255 (L858R) was obtained from the American Type Culture Collection. The NCI-H3255 cells were maintained in BEBM media (Lonza; CC-3171), containing 10% fetal bovine serum (FBS) (Gibco; 10099-141), supplemented with BEGM kit (Lonza; CC-4175). The human lung cell line PC-9 (Exon 19 deletion EGFR) was obtained from the American Type Culture Collection. PC-9 cells were maintained in RPMI 1640 (Gibco; 22400-089), containing 10% fetal bovine serum. The human lung cell line NCI-H838 (EGFR wild type) was obtained from the American Type Culture Collection. NCI-H838 cells were maintained in RPMI 1640 (Gibco; 22400-089), containing 10% fetal bovine serum.

All cells were grown in a humidified incubator at 37° C. with 5% $CO_2$. Assays to measure cellular phosphorylation of endogenous p-EGFR in cell lysates were carried out according to the protocol described in the PathScan® Phospho-EGF Receptor (Tyr1068) Sandwich ELISA Kit (Cell Signalling kit catalogue number #7240).

100 µL of cells were seeded (32000 cells/well) in RPMI 1640+1% fetal bovine serum in Corning Costar, 96 well cell culture plates and incubated at 37° C. with 5% $CO_2$ iii overnight. Cells were acoustically dosed using a Tecan, with compounds serially diluted in 100% DMSO. Cell plates were incubated for a further 4 h after the compounds were added, (for NCI-H838: rhEGF (R&D catalogue number#236-EG) was added to cell plate with final concentration 100 ng/ml rhEGF to stimulate 5 minutes), then following aspiration of medium, 110 µL IP lysis buffer (IP lysis buffer: add 1:100 phosphatase inhibitor cocktail 2&3 (Sigma catalogue number P5726&P0044), 1:100 protease inhibitor cocktail (Sigma catalogue number P8340) to Pierce IP lysis buffer (Thermo catalogue number #87788)) was added to each well. The plates were put at 4° C. with rotation 300 rpm for 0.5-1 hour. 100 µl/well of cell lysis was transferred to coated plates (Cell Signalling kit catalogue number#7240) and incubated overnight at 4° C. with rotation 300 rpm. The plates we taken from 4° C. to 37° C. with rotation 300 rpm for 1 hour. Following aspiration and washing of the plates with 1× wash buffer, 100 μl of detection antibody (Cell Signalling kit catalogue number#7240) was added to each well. The plate was sealed with tape and incubated for 2 hours at 37° C. with rotation 300 rpm. Following aspiration and washing of the plates with 1× wash buffer, 100 μl of HRP-linked secondary antibody (Cell Signalling kit catalogue number#7240) was added to each well. The plate was sealed with tape and incubated for 1 hour at 37° C. with rotation 300 rpm. Following aspiration and washing of the plates with 1× wash buffer, 100 μl of TMB substrate (Cell Signalling kit, catalogue number#7240) was added to each well. The plate was sealed with tape and incubated for 30 minutes at 37° C. with 300 rpm. 100 μl stop solution (Cell Signalling kit catalogue number#7240) was added to the plates and absorbance read at 450 nm within 30 minutes on SpectraMax M5e plate reader.

The data obtained with each compound was exported into a suitable software package (such as H-BASE) to perform curve fitting analysis. From this data an $IC_{50}$ value was determined by calculation of the concentration of compound that is required to give a 50% effect.

The assay data (μM) in Assay 1 for the Examples of this application as well as that obtained for gefitinib and erlotinib are shown in the table below (where n=the number of times the experiment was repeated):

| Compound | $IC_{50}$ (NCI-H3255) | $IC_{50}$ (PC-9) | $IC_{50}$ (NCI-H838) |
|---|---|---|---|
| Example 1 | 0.0072 ± 0.0013 (n = 12) | 0.0074 ± 0.0013 (n = 12) | 0.065 ± 0.009 (n = 13) |
| Example 3 | 0.005 (n = 1) | 0.008 (n = 1) | 0.04 (n = 1) |
| Example 4 | 0.001 (n = 1) | 0.004 (n = 1) | 0.04 (n = 1) |
| gefitinib | 0.0065 ± 0.002 (n = 42) | 0.0062 ± 0.0019 (n = 42) | 0.03 ± 0.01 (n = 42) |
| erlotinib | 0.0081 ± 0.0019 (n = 10) | 0.0061 ± 0.0019 (n = 10) | 0.033 ± 0.007 (n = 10) |

This shows that Example 1, Example 2, and Example 3 have comparable potency to gefitinib and erlotinib.

Assay 2: Brain Blood Barrier Penetration Assay

Both $K_{p,uu\ brain}$ and $K_{p,uu\ CSF}$ should be the main parameters measured and optimized in CNS drug discovery (Di L et al., *Journal of Medicinal Chemistry* [2013], 56: 2-12). $K_{p,uu\ brain}$, the relationship between concentrations of unbound drug in brain and in blood, predicts drug action on metastatic tumors in brain Leptomeningeal metastasis (LM) results from metastatic spread of cancer to the leptomeninges, giving rise to central nervous system dysfunction. $K_{p,uu\ CSF}$ represents the distribution of drug in CSF as compared to that in blood, which drives drug response during leptomeningeal metastasis treatment.

In vitro blood and brain binding assay was carried out on a HT-Dialysis plate (Gales Ferry, Conn.) with semi-permeable membrane. Diluted blood (1:1 with DPBS pH7.4) and brain homogenate (1:3 with DPBS pH7.4) were spiked with 5 μM test compound (in triplicate) and dialyzed against equal volume of 150 μL 100 mM PBS buffer (pH7.4) at 37° C. for 4 hours in a slowly rotated plate. At the end of incubation, a 50 μL aliquot from the receiver side and a 5 μL from the donor chamber were taken. The 5 μL sample was further diluted with 45 μL of blank blood or brain homogenate. Paired samples were matrix-matched with either buffer or blank blood/brain homogenate and mixed for 2 min, and then precipitated with 150 μL cold acetonitrile with 100 ng/mL tolbutamide as internal standard. After centrifuging at 4000 rpm for 20 min, supernatant was diluted with 0.1% formic acid aqueous solution and analyzed for LC/MS/MS (API 4000, Applied Biosystems, Foster City). Unbound fraction (fu) of test compound in the brain homogenate and diluted blood were calculated by the ratio of the buffer side response to the brain homogenate/blood side response, and unbound fraction ($f_{u,bl}$ and $f_{u,br}$) of test compound in non-diluted blood and tissue were calculated from measured fu in homogenate and diluted blood with the following equation: $f_{u,bl}\ (f_{u,br})=(1/D)/[(1/fu-1)+1/D)]$. D is dilution factor.

A Short oral absorption (SOA) model is an in-vivo screening model to identify brain penetration of a compound. Six male Han Wistar rats purchased from Beijing Vital River were orally dosed with the compound at 2 mg/kg in 1% methylcellulose. At 0.25, 0.5, 1, 2, 4 and 7 hour post-dose, cerebral spinal fluid (CSF) was collected from cisterna magna, and blood samples (>60 μL/time point/each site) were collected via cardiac puncture, into separate EDTA coagulated tubes, and then immediately diluted with 3-fold volume of water. Brain tissue was harvested and homogenized in 3× volume of 100 mM phosphate buffered saline (pH7.4). All samples were stored at ~−70° C. prior to LC/MS/MS analysis.

Standards were prepared by spiking blank blood, brain homogenate and artificial CSF covering 0.2 to 500 ng/mL. Homogenized brain tissue along with blood samples were precipitated by adding 3-fold volume of cold acetonitrile containing internal standard (40 ng/mL Dexamethasone and 40 ng/mL Diclofenac), and 10 μL of CSF samples were precipitated with 100 μL of cold acetonitrile containing internal standard. After 2 min vortex and 5 min centrifugation at 14,000 rpm, supernatant was analyzed by LC/MS/MS (API 4000, Applied Biosystems, Foster City). Two sets of standard curves were run at the beginning and end of each batch from blood sample analysis. For brain and CSF samples, one standard curve was analyzed along with test samples.

Total brain levels, expressed as brain/blood ratio ($K_{p,brain}$) were measured by $AUC_{brain}/AUC_{blood}$ in rodents after oral administration. Free fraction of test compound in biological matrix was determined by in vitro blood and brain binding assay. $K_{p,uu\ brain}$ and $K_{p,uu\ CSF}$ were calculated by the following equation: $K_{p,uu\ brain}=AUC_{brain}/AUC_{blood}\times(f_{u,brain}/f_{u,blood})$ and $K_{p,uu\ CSF}=AUC_{CSF}/AUC_{blood}\times f_{u,blood}$ The assay data in Assay 2 for the Examples of this application as well as data obtained for sapitinib (freebase form) is shown in the table below:

| Compound | $K_{p,uu\ brain}$ | $K_{p,uu\ CSF}$ |
|---|---|---|
| Example 1 | 0.8-1.3 (n = 2) | 1.0-1.3 (n = 2) |
| Example 3 | 1.6 (n = 1) | 2.6 (n = 1) |
| sapitinib | 0.13 (n = 1) | Below quantification limit | demonstrating the superior brain barrier penetration properties of the compounds of the present invention, when compared to sapitinib.

According to a further aspect of the invention there is provided a pharmaceutical composition which comprises a compound of formula (I), or a pharmaceutically acceptable salt thereof, as defined hereinbefore, in association with a pharmaceutically acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository. Particularly the composition may be in a form suitable for oral administration.

In general the above compositions may be prepared in a conventional manner using conventional excipients.

The compound of formula (I), or a pharmaceutically acceptable salt thereof, will be administered to a warm-blooded animal at a unit dose within the range 0.01-2000 mg/kg, particularly 2.5-1000 mg/kg, particularly 5-500 mg/kg, and this should provide a therapeutically effective dose. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of formula (I), or a pharmaceutically acceptable salt thereof, as defined hereinbefore for use in a method of treatment of the human or animal body by therapy.

As a result of its activating mutant EGFR inhibitory activity, the compounds of formula (I), or a pharmaceutically acceptable salt thereof, are expected to be useful in the treatment of diseases or medical conditions mediated alone or in part by activating mutant EGFR, for example cancer. The types of cancers which may be susceptible to treatment using the compounds of formula (I), or a pharmaceutically acceptable salt thereof, include, but are not limited to, ovarian cancer, cervical cancer, colorectal cancer, breast cancer, pancreatic cancer, glioma, glioblastoma, melanoma, prostate cancer, leukaemia, lymphoma, non-Hodgkins lymphoma, lung cancer, hepatocellular cancer, gastric cancer, gastrointestinal stromal tumour, thyroid cancer, bile duct cancer, endometrial cancer, renal cancer, anaplastic large cell lymphoma, acute myeloid leukaemia, multiple myeloma, melanoma and mesothelioma. In a particular embodiment of the invention, the type of cancer which may be susceptible to treatment using the compound of formula (I), or a pharmaceutically acceptable salt thereof is non-small-cell lung cancer (NSCLC). In a further particular embodiment the NCSLC cells in the warm blooded animal possess or have previously been shown to possess activation mutations in the EGFR gene.

The compound of formula (I), or a pharmaceutically acceptable salt thereof, is useful in the treatment of disease states in which activating mutant EGFR is implicated. In one aspect of the invention where activating mutant EGFR is referred to this refers one or more mutations in the ATP-binding site (kinase domain) of the EGFR gene, particularly around Exons 18-21, such as those described in WO 2005/094357. In one aspect of the invention where activating mutant EGFR is referred to this refers to L858R activating mutant EGFR and/or Exon 19 deletion activating mutant EGFR. In one aspect of the invention where activating mutant EGFR is referred to this refers to L858R activating mutant EGFR and Exon 19 deletion activating mutant EGFR. In one aspect of the invention where activating mutant EGFR is referred to this refers to L858R activating mutant EGFR. In another aspect of the invention where activating mutant EGFR is referred to this refers to Exon 19 deletion activating mutant EGFR.

It is envisaged that for the methods of treatment of cancer mentioned herein, the compounds of formula (I), or a pharmaceutically acceptable salt thereof, will be administered to a mammal, more particularly a human being. Similarly, the uses of the compounds of formula (I), or a pharmaceutically acceptable salt thereof, for the treatment of cancer mentioned herein, it is envisaged that the compounds of formula (I), or a pharmaceutically acceptable salt thereof, will be administered to a mammal, more particularly a human being.

According to another aspect of the invention, there is therefore provided the compounds of formula (I), or a pharmaceutically acceptable salt thereof, as defined hereinbefore for use as a medicament.

According to a further aspect of the invention there is provided the use of a compound of formula (I), or a pharmaceutically acceptable salt thereof, as defined hereinbefore in the manufacture of a medicament for the inhibition of activating mutant EGFR in a warm-blooded animal such as man.

According to this aspect of the invention there is provided the use of a compound of formula (I), or a pharmaceutically acceptable salt thereof, as defined hereinbefore in the manufacture of a medicament for the production of an anti-cancer effect in a warm-blooded animal such as man.

According to a further feature of the invention, there is provided the use of a compound of formula (I), or a pharmaceutically acceptable salt thereof, as defined hereinbefore in the manufacture of a medicament for use in the treatment of ovarian cancer, cervical cancer, colorectal cancer, breast cancer, pancreatic cancer, glioma, glioblastoma, melanoma, prostate cancer, leukaemia, lymphoma, non-Hodgkins lymphoma, lung cancer, hepatocellular cancer, gastric cancer, gastrointestinal stromal tumour, thyroid cancer, bile duct cancer, endometrial cancer, renal cancer, anaplastic large cell lymphoma, acute myeloid leukaemia, multiple myeloma, melanoma and mesothelioma.

According to a further feature of the invention, there is provided the use of a compound of formula (I), or a pharmaceutically acceptable salt thereof, as defined hereinbefore in the manufacture of a medicament for use in the treatment of NSCLC.

According to a further feature of this aspect of the invention there is provided a method of inhibiting activating mutant EGFR in a warm-blooded animal, such as man, in need of such treatment which comprises administering to said animal an effective amount of a compound of formula (I), or a pharmaceutically acceptable salt thereof, as defined hereinbefore.

According to a further feature of this aspect of the invention there is provided a method for producing an anti-cancer effect in a warm-blooded animal, such as man, in need of such treatment which comprises administering to said animal an effective amount of a compound of formula (I), or a pharmaceutically acceptable salt thereof, as defined hereinbefore.

According to a further feature of this aspect of the invention there is provided a method for producing an anti-cancer effect in a warm-blooded animal, such as man, in need of such treatment which comprises (1) determining whether or not the warm blooded animal has an activating EGFR mutation in the tumour cell and (2) and if so administering to said animal an effective amount of the compound of formula (I), or a pharmaceutically acceptable salt thereof, as defined hereinbefore.

According to an additional feature of this aspect of the invention there is provided a method of treating ovarian cancer, cervical cancer, colorectal cancer, breast cancer, pancreatic cancer, glioma, glioblastoma, melanoma, prostate cancer, leukaemia, lymphoma, non-Hodgkins lymphoma, lung cancer, hepatocellular cancer, gastric cancer, gastrointestinal stromal tumour, thyroid cancer, bile duct cancer, endometrial cancer, renal cancer, anaplastic large cell lymphoma, acute myeloid leukaemia, multiple myeloma, melanoma and mesothelioma, in a warm-blooded animal, such as man, in need of such treatment which comprises administering to said animal an effective amount of a compound of formula (I), or a pharmaceutically acceptable salt thereof, as defined hereinbefore.

According to an additional feature of this aspect of the invention there is provided a method of treating NSCLC, in a warm-blooded animal, such as man, in need of such treatment which comprises administering to said animal an effective amount of a compound of formula (I), or a pharmaceutically acceptable salt thereof, as defined hereinbefore.

According to a further aspect of the invention there is provided a compound of formula (I), or a pharmaceutically acceptable salt thereof, as defined hereinbefore for use in inhibiting activating mutant EGFR in a warm-blooded animal such as man.

According to this aspect of the invention there is provided a compound of formula (I), or a pharmaceutically acceptable salt thereof, as defined hereinbefore for use in the production of an anti-cancer effect in a warm-blooded animal such as man.

According to a further feature of the invention, there is provided a compound of formula (I), or a pharmaceutically acceptable salt thereof, as defined hereinbefore for use in the treatment of ovarian cancer, cervical cancer, colorectal cancer, breast cancer, pancreatic cancer, glioma, glioblastoma, melanoma, prostate cancer, leukaemia, lymphoma, non-Hodgkins lymphoma, lung cancer, hepatocellular cancer, gastric cancer, gastrointestinal stromal tumour, thyroid cancer, bile duct cancer, endometrial cancer, renal cancer, anaplastic large cell lymphoma, acute myeloid leukaemia, multiple myeloma, melanoma and mesothelioma.

According to a further feature of the invention, there is provided a compound of formula (I), or a pharmaceutically acceptable salt thereof, as defined hereinbefore for use in the treatment of NSCLC.

In a further aspect of the invention there is provided a pharmaceutical composition which comprises a compound of formula (I), or a pharmaceutically acceptable salt thereof, as defined hereinbefore in association with a pharmaceutically acceptable diluent or carrier for use in inhibiting activating mutant EGFR in a warm-blooded animal such as man.

In a further aspect of the invention there is provided a pharmaceutical composition which comprises a compound of formula (I), or a pharmaceutically acceptable salt thereof, as defined hereinbefore in association with a pharmaceutically acceptable diluent or carrier for use in the production of an anti-cancer effect in a warm-blooded animal such as man.

In a further aspect of the invention there is provided a pharmaceutical composition which comprises a compound of formula (I), or a pharmaceutically acceptable salt thereof, as defined hereinbefore in association with a pharmaceutically acceptable diluent or carrier for use in the treatment of ovarian cancer, cervical cancer, colorectal cancer, breast cancer, pancreatic cancer, glioma, glioblastoma, melanoma, prostate cancer, leukaemia, lymphoma, non-Hodgkins lymphoma, lung cancer, hepatocellular cancer, gastric cancer, gastrointestinal stromal tumour, thyroid cancer, bile duct cancer, endometrial cancer, renal cancer, anaplastic large cell lymphoma, acute myeloid leukaemia, multiple myeloma, melanoma and mesothelioma in a warm-blooded animal such as man.

In a further aspect of the invention there is provided a pharmaceutical composition which comprises a compound of formula (I), or a pharmaceutically acceptable salt thereof, as defined hereinbefore in association with a pharmaceutically acceptable diluent or carrier for use in the treatment of NSCLC in a warm-blooded animal such as man.

In any of the aspects or embodiments mentioned herein where cancer is mentioned said cancer may be selected from ovarian cancer, cervical cancer, colorectal cancer, breast cancer, pancreatic cancer, glioma, glioblastoma, melanoma, prostate cancer, leukaemia, lymphoma, non-Hodgkins lymphoma, lung cancer, hepatocellular cancer, gastric cancer, gastrointestinal stromal tumour, thyroid cancer, bile duct cancer, endometrial cancer, renal cancer, anaplastic large cell lymphoma, acute myeloid leukaemia, multiple myeloma, melanoma and mesothelioma.

In any of the aspects or embodiments mentioned herein where cancer is mentioned, particularly said cancer may be selected from lung cancer. In a further aspect, particularly said cancer may be selected from non-small-cell lung cancer. In a further aspect, particularly said cancer may be selected from non-metastatic non-small-cell lung cancer. In a further aspect, particularly said cancer may be selected from metastatic non-small-cell lung cancer.

The compound of the present invention may be applied in the adjuvant and/or $1^{st}$ line and/or $2^{nd}$ line treatment settings of NSCLC patients carrying activating mutant EGFR, with and without CNS metastasis, particularly brain metastasis and/or leptomeningeal metastases.

In another aspect the cancer is in a non metastatic state.

In another aspect the cancer is in a metastatic state.

In another aspect of the invention particularly the metastasis are CNS metastases.

In another aspect, particularly the CNS metastases are brain metastases.

In another aspect, particularly the CNS metastases are leptomeningeal metastases.

Certain NSCLC patients with CNS metastasis, particularly brain metastasis and/or leptomeningeal metastases, exhibit CNS symptoms, such as headache and vomiting. For these patients, whole brain radiation therapy (WBRT) may be used to improve these symptoms. The compound of the present invention may be able to enhance the anti-tumour effect of WBRT as well as to further improve CNS symptoms when used in combination with WBRT.

The activating mutant EGFR activity treatment defined hereinbefore may be applied as a sole therapy or may involve, in addition to the compound of the invention, conventional surgery or radiotherapy (for example WBRT as described hereinabove) or chemotherapy. Such chemotherapy may include one or more of the following anti-tumour agents:—

(i) an anti-CTLA-4 antibody;

(ii) 6-(4-bromo-2-chloro-phenylamino)-7-fluoro-3-methyl-3H-benzoimidazole-5-carboxylic acid (2-hydroxyethoxy)-amide (as disclosed in WO 2007/076245) or a pharmaceutically acceptable salt thereof;

(iii) an anti-PD-L1 antibody;

(iv) 1-[(1S)-1-(imidazo[1,2-a]pyridin-6-yl)ethyl]-6-(1-methyl-1H-pyrazol-4-yl)-1H-[1,2,3]triazolo[4,5-b]pyrazine (Compound 270 of WO 2011/079804) or a pharmaceutically acceptable salt thereof;

(v) an anti-PD-1 antibody; or (vi) an OX40 agonist antibody.

Particularly an anti-CTLA-4 antibody is tremelimumab (as disclosed in U.S. Pat. No. 6,682,736). In another aspect of the invention, particularly an anti-CTLA-4 antibody is ipilimumab (marketed by Bristol Myers Squib as YERVOY®).

Particularly "6-(4-bromo-2-chloro-phenylamino)-7-fluoro-3-methyl-3H-benzoimidazole-5-carboxylic acid (2-hydroxy-ethoxy)-amide (as disclosed in WO 2007/076245) or a pharmaceutically acceptable salt thereof" is the hydrogen sulphate salt of 6-(4-bromo-2-chloro-phenylamino)-7-fluoro-3-methyl-3H-benzoimidazole-5-carboxylic acid (2-hydroxy-ethoxy)-amide. More particularly the hydrogen sulphate salt is 1:1 compound:$H_2SO_4$.

Particularly an anti-PD-L1 antibody is an antibody as disclosed in US 20130034559 (MedImmune). In another aspect of the invention particularly an anti-PD-L1 antibody is an antibody as disclosed US 2010/0203056 (Genentech/Roche). In another aspect of the invention particularly an anti-PD-L1 antibody is an antibody as disclosed US 20090055944 (Medarex). In another aspect of the invention particularly an anti-PD-L1 antibody is an antibody as disclosed US 20130323249 (Sorrento Therapeutics).

Particularly an anti-PD-1 antibody is MRK-3475 as disclosed in WO 2009/114335 and U.S. Pat. No. 8,168,757 (Merck). In another aspect of the invention particularly is Nivolumab, an anti-PD-1 antibody as disclosed in WO 2006/121168 or U.S. Pat. No. 8,008,449 (Medarex). In another aspect of the invention particularly an anti-PD-1 antibody is an antibody as disclosed in WO2009/101611 (CureTech). In another aspect of the invention particularly an anti-PD-1 antibody is an antibody as disclosed in WO2012/145493 (Amplimmune). In another aspect of the invention particularly an anti-PD-1 antibody is an antibody as disclosed in U.S. Pat. No. 7,488,802 (Wyeth/MedImmune).

Particularly an anti-OX40 antibody is an antibody as disclosed in US20110123552 (Crucell). In another aspect of the invention particularly an anti-PD-1 antibody is an antibody as disclosed in US 20130280275 (Board of Regents, Univ. of Texas). In another aspect of the invention particularly an anti-PD-1 antibody is an antibody as disclosed in WO 99/42585 (Agonox) and WO 95/12673 and WO 95/21915.

According to this aspect of the invention there is provided a combination suitable for use in the treatment of cancer comprising a compound of formula (I) as defined hereinbefore or a pharmaceutically acceptable salt thereof and any one of the anti tumour agents listed under (i)-(iv) above.

Therefore in a further aspect of the invention there is provided a compound of formula (I) or a pharmaceutically acceptable salt thereof in combination with an anti-tumour agent selected from one listed under (i)-(iv) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of formula (I) or a pharmaceutically acceptable salt thereof in combination with an anti-tumour agent selected from one listed under (i)-(iv) herein above, in association with a pharmaceutically acceptable diluent or carrier.

According to a further aspect of the invention there is provided a pharmaceutical composition which comprises a compound of formula (I) or a pharmaceutically acceptable salt thereof in combination with an anti-tumour agent selected from one listed under (i)-(iv) herein above, in association with a pharmaceutically acceptable diluent or carrier for use in producing activating mutant EGFR activity.

According to a further aspect of the invention there is provided a pharmaceutical composition which comprises a compound of formula (I) or a pharmaceutically acceptable salt thereof in combination with an anti-tumour agent selected from one listed under (i)-(iv) herein above, in association with a pharmaceutically acceptable diluent or carrier for use in producing an anti-cancer effect.

According to a further aspect of the invention there is provided a pharmaceutical composition which comprises a compound of formula (I) or a pharmaceutically acceptable salt thereof in combination with an anti-tumour agent selected from one listed under (i)-(iv) herein above, in association with a pharmaceutically acceptable diluent or carrier for use in treating ovarian cancer, cervical cancer, colorectal cancer, breast cancer, pancreatic cancer, glioma, glioblastoma, melanoma, prostate cancer, leukaemia, lymphoma, non-Hodgkins lymphoma, lung cancer, hepatocellular cancer, gastric cancer, gastrointestinal stromal tumour, thyroid cancer, bile duct cancer, endometrial cancer, renal cancer, anaplastic large cell lymphoma, acute myeloid leukaemia, multiple myeloma, melanoma and mesothelioma.

According to a further aspect of the invention there is provided a pharmaceutical composition which comprises a compound of formula (I) or a pharmaceutically acceptable salt thereof in combination with an anti-tumour agent selected from one listed under (i)-(iv) herein above, in association with a pharmaceutically acceptable diluent or carrier for use in treating NSCLC.

According to a further aspect of the present invention there is provided a kit comprising a compound of formula (I) or a pharmaceutically acceptable salt thereof in combination with an anti-tumour agent selected from one listed under (i)-(iv) herein above.

According to a further aspect of the present invention there is provided a kit comprising:

a) a compound of formula (I) or a pharmaceutically acceptable salt thereof in a first unit dosage form;

b) an anti-tumour agent selected from one listed under (i)-(iv) herein above; in a second unit dosage form; and c) container means for containing said first and second dosage forms.

In addition to their use in therapeutic medicine, the compounds of formula (I), or a pharmaceutically acceptable salt thereof, are also useful as pharmacological tools in the development and standardisation of in vitro and in vivo test systems for the evaluation of the effects of activating mutant EGFR inhibitory activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated in the following Examples in which, generally:

(i) in general, the course of reactions were followed by liquid chromatography mass spectrometry (LCMS) or thin later chromatography (TLC); the reaction times that are given are not necessarily the minimum attainable;

(ii) when necessary, organic solutions were dried over anhydrous magnesium sulfate or anhydrous sodium sulfate, work-up procedures were carried out using traditional layer separating techniques, evaporations were carried out either by rotary evaporation under reduced pressure or in a Genevac HT-4/EZ-2.

(iii) yields, where present, are not necessarily the maximum attainable, and when necessary, reactions were repeated if a larger amount of the reaction product was required;

(iv) in general, the structures of the end-products were confirmed by nuclear magnetic resonance (NMR) and/or mass spectral techniques; electrospray mass spectral data were obtained using a Waters ZMD or Waters ZQ LC/mass spectrometer acquiring both positive and negative ion data, generally, only ions relating to the parent structure are reported; proton NMR chemical shift values were measured on the delta scale at 400 MHz using a Bruker NMR spectrometer or a Varian NMR spectrometer. The following abbreviations have been used: s, singlet; d, doublet; pd, partial doublet; t, triplet; q, quartet; m, multiplet; br, broad. Exchangeable protons are not always observed or reported in the NMR of end-products due to exchange with deuterated solvent or advantageous deuterated water in the solvent or the signal is poorly resolved and/or very broad;

(v) intermediates were not necessarily fully purified but their structures and purity were assessed by TLC, analytical HPLC and/or NMR analysis;

(vi) unless otherwise stated, column chromatography (by the flash procedure) and medium pressure liquid chromatography (MPLC) were performed on Merck Kieselgel silica (Art. 9385) or by using pre-packed silica cartridges on semi-automated flash chromatography equipment (for example a CombiFlash Companion); and (vii) the following abbreviations have been used:
Boc tert-butyloxycarbonyl;
$CD_3OD$ deuteromethanol;
DMSO-$d_6$ hexadeuterodimethylsulfoxide;
$CDCl_3$ deuterochlorform;
PE petroleum ether;
IPA isopropanol;
iPrOAc isopropyl acetate;
MTBE methyl tert-butyl ether;
DCM dichloromethane;
THF tetrahydrofuran;
RT room temperature;
MeOH methanol;
EtOH ethanol; and
EtOAc ethyl acetate.

X-Ray Powder Diffraction

Analytical Instrument: Panalytical Empyrean. The X-ray powder diffractogram was determined by mounting a sample of the crystalline material on a Si single crystal holder and spreading out the sample into a thin layer with the aid of a microscope slide. The 2θ position was calibrated against Panalytical 640 Si powder standard. The sample irradiated with X-rays generated by a copper long-fine focus tube operated at 45 kV and 40 mA with a wavelength of Kα1=1.540598 angstroms and Kα2=1.544426 angstroms (Kα2/Kα1 intensity ratio is 0.50). The collimated X-ray source was passed through a programmed divergence slit set at 10 mm and the reflected radiation directed through a 5.5 mm antiscatter slit. The sample was exposed for 12.7 seconds per 0.0167° 2-theta increment (continuous scan mode) over the range 3 degrees to 40 degrees 2-theta in theta-theta mode. The running time was 3 minutes and 57 seconds. The instrument was equipped with a RTMS detector (X'Celerator). Control and data capture was by means of a Dell Optiplex 780 XP operating with data collector software. Persons skilled in the art of X-ray powder diffraction will realize that the relative intensity of peaks can be affected by, for example, grains above 30 microns in size and non-unitary aspect ratios that may affect analysis of samples. The skilled person will also realize that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

Differential Scanning Calorimetry

Analytical Instrument: TA Instruments Q200 or Q2000 DSC. Typically less than 5 mg of material contained in a standard aluminium pan fitted with a lid was heated over the temperature range 25° C. to 300° C. at a constant heating rate of 10° C. per minute. A purge gas using nitrogen was used—flow rate 50 ml per minute.

Intermediate 1

5-Hydroxy-4-methoxy-2-nitrobenzoic acid

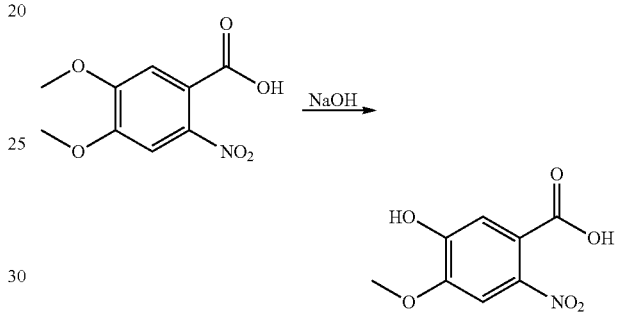

4,5-Dimethoxy-2-nitrobenzoic acid (145 g, 0.639 mol) was dissolved in a solution of sodium hydroxide (6N, 600 mL) and heated at 100° C. for 3 h. The mixture was cooled to RT, and poured into a mixture of concentrated hydrochloric acid and crushed ice (pH<2). The mixture was filtered, and the filter cake was dried to give Intermediate 1 (149 g, crude) as a yellow solid, which was used without further purification. $^1$H NMR (DMSO-$d_6$ 400 MHz): δ 7.34 (s, 1H), 6.89 (s, 1H), 3.80 (s, 3H).

Intermediate 2

2-Amino-5-hydroxy-4-methoxybenzoic acid

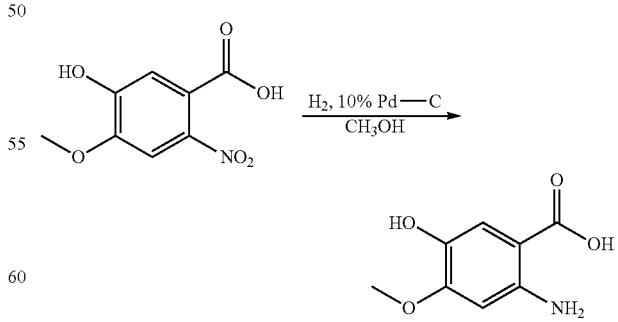

A mixture of Intermediate 1 (50 g, 93.85 mmol) and 10% Pd/C (5 g) in MeOH (1.2 L) was stirred under $H_2$ atmosphere (50 psi) at RT for 4 h. The mixture was filtered and washed with MeOH (10×1 L). The combined MeOH extracts were concentrated to afford Intermediate 2 (27.7 g, 64% yield) as black solid which was used without further purification.

Intermediate 3

7-Methoxyquinazoline-4,6-diol

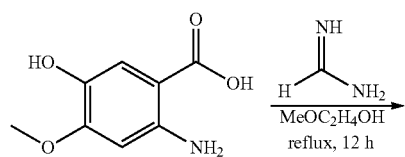

To a suspension of Intermediate 2 (88 g, 0.48 mol) in 2-methoxyethanol (2 L) was added formamidine (101 g, 0.96 mol) and the reaction mixture was refluxed overnight. The reaction mixture was concentrated, diluted with water (1.5 L) and neutralized (to pH=7) with ammonia. The mixture was filtered and the precipitate was washed with water. The precipitate was dried under reduced pressure to afford Intermediate 3 as a brown solid (62 g, 67% yield). $^1$H NMR (DMSO-$d_6$ 400 MHz): δ 7.89 (s, 1H), 7.36 (s, 1H), 7.08 (s, 1H), 3.88 (s, 3H).

Intermediate 4

4-Hydroxy-7-methoxyquinazolin-6-yl acetate

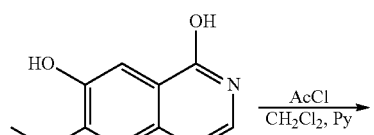

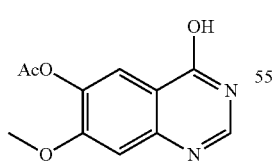

To a suspension of Intermediate 3 (52 g, 0.27 mol) and pyridine (53.6 g, 0.68 mol) in anhydrous DCM (1 L) was added acetic chloride (52.9 g, 0.68 mol) drop-wise and the mixture was stirred overnight at RT. The mixture was poured into water (1 L) and extracted with DCM several times. The combined organic layers were washed with brine, dried over Na$_2$SO$_4$, concentrated to afford Intermediate 4 as a black solid (63.2 g, 100% yield). $^1$H NMR (DMSO-$d_6$ 400 MHz): δ 8.62 (s, 1H), 7.88 (s, 1H), 7.37 (s, 1H), 3.95 (s, 3H), 2.74 (s, 3H).

Intermediate 5

4-Chloro-7-methoxyquinazolin-6-yl acetate

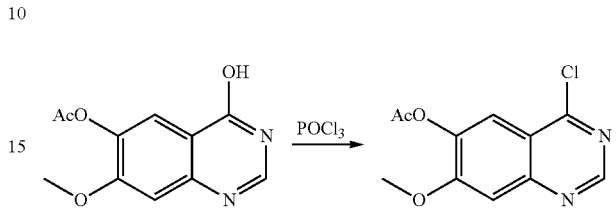

A suspension of Intermediate 4 (75.6 g, 0.323 mol) in POCl$_3$ (287 mL) was heated to refluxed for 0.5 h. The reaction mixture was concentrated and diluted with DCM (500 mL), poured into water (500 mL), filtered and washed with DCM. The combined organic layers were washed with brine, dried over Na$_2$SO$_4$ and concentrated. Purification by chromatography (PE/EtOAc=1/1) gave Intermediate 5 (55 g, 67% yield) as white solid. $^1$H NMR (CDCl$_3$ 400 MHz): δ 8.95 (s, 1H), 7.90 (s, 1H), 7.43 (s, 1H), 4.02 (s, 1H), 2.39 (s, 1H).

Intermediate 6

4-[(3-Chloro-2-fluorophenyl)amino]-7-methoxyquinazolin-6-yl acetate

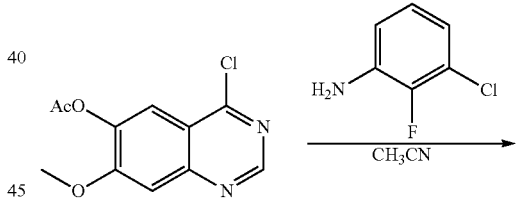

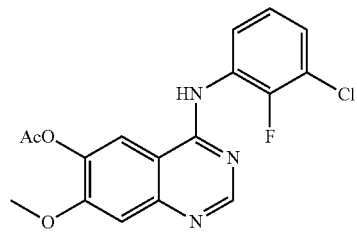

To a suspension of Intermediate 5 (100 g, 0.396 mol) in acetonitrile (4 L) was added 2-fluoro-3-chloroaniline (60.5 g, 0.416 mol) and the reaction mixture was heated to 80° C. overnight. The precipitate was collected by filtration and dried in vacuo to afford Intermediate 6 (181 g, 80% purity) as white solid which was used for next step directly without purification. $^1$H NMR (DMSO-$d_6$ 400 MHz): δ 8.93 (s, 1H), 8.82 (s, 1H), 7.67-7.63 (m, 1H), 7.59 (s, 1H), 7.56-7.52 (m, 1H), 7.39-7.35 (m, 1H), 4.02 (s, 3H), 2.39 (s, 3H).

Intermediate 7

4-[(3-Chloro-2-fluorophenyl)amino]-7-methoxyquinazolin-6-ol

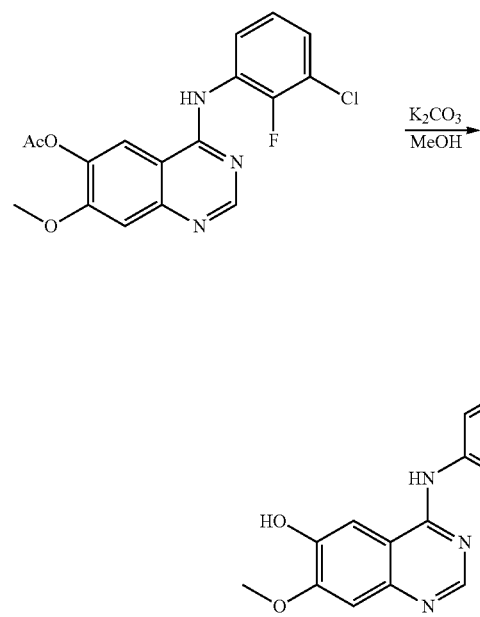

To a solution of Intermediate 6 (181 g, 0.396 mol) in MeOH (2 L) was added potassium carbonate (138 g, 1 mol) and the reaction mixture was stirred at RT overnight. The reaction mixture was filtered and the solid washed with MeOH. The filtrate was concentrated in vacuo to afford Intermediate 7 (280 g, 60% purity, contained potassium carbonate). $^1$H NMR (DMSO-d$_6$ 400 MHz): δ 8.01 (s, 1H), 7.61-7.58 (m, 1H), 7.27-7.24 (m, 1H), 7.17-7.13 (m, 1H), 6.95 (s, 1H), 6.83 (s, 1H), 3.79 (s, 3H).

Intermediate 8 tert-Butyl (3R)-4-(chlorocarbonyl)-3-methylpiperazine-1-carboxylate

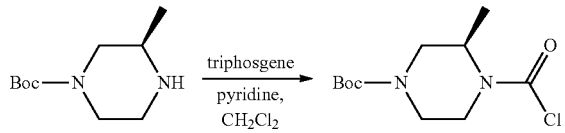

To a mixture of triphosgene (23 g, 75 mmol) in anhydrous DCM (250 mL) was added pyridine (18 g, 225 mmol) dropwise followed by addition of tert-butyl (3R)-3-methylpiperazine-1-carboxylate (15 g, 75 mmol) at 0° C. The mixture was stirred overnight at RT. TLC showed the starting material had been consumed. The mixture was concentrated to afford Intermediate 8 as yellow solid, which was used without further purification.

Intermediate 9

4-tert-Butyl 1-{4-[(3-chloro-2-fluorophenyl)amino]-7-methoxyquinazolin-6-yl}(2R)-2-methylpiperazine-1,4-dicarboxylate

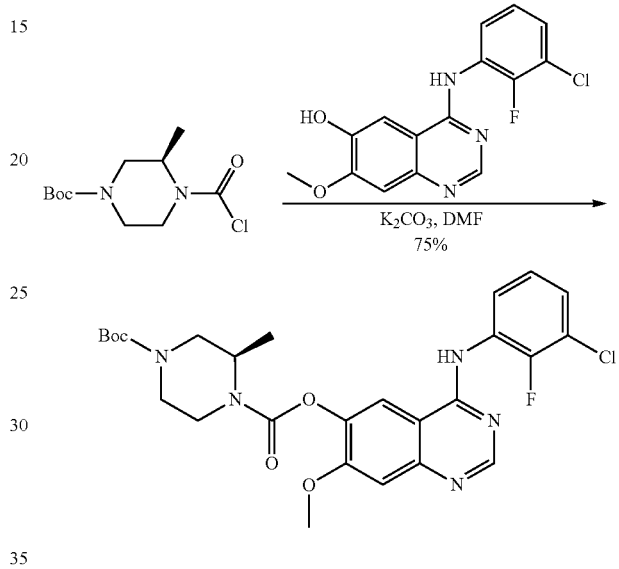

A mixture of Intermediate 7 (19.2 g, 60 mmol), Intermediate 8 prepared according to the above procedure and potassium carbonate (16.6 g, 120 mmol) in anhydrous DMF (300 mL) was stirred overnight at RT. The reaction mixture was poured into water (250 mL) and filtered, and the filter cake was dried under vacuum to afford Intermediate 9 (25 g, 75% yield) as yellow solid. HPLC: t$_R$=2.68 min in 10-80AB_6 min chromatography (Ultimate XB-C18, 3.0*50 mm, 3 um). LCMS: t$_R$=0.792 min in 5-95AB_1.5 min chromatography (Welch Xtimate C18, 2.1*30 mm, 3 um), MS (ESI) m/z 546.0 [M+H]$^+$.

Intermediate 10

4-[(3-Chloro-2-fluorophenyl)amino]-7-methoxyquinazolin-6-yl (2R)-2-methylpiperazine-1-carboxylate

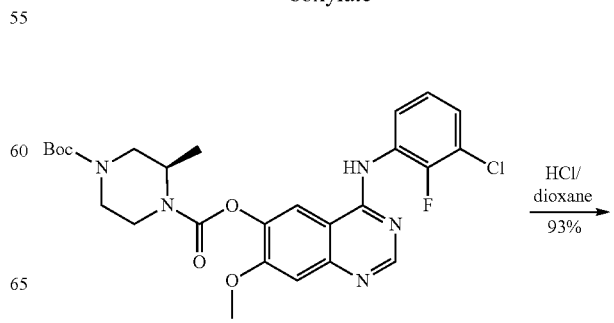

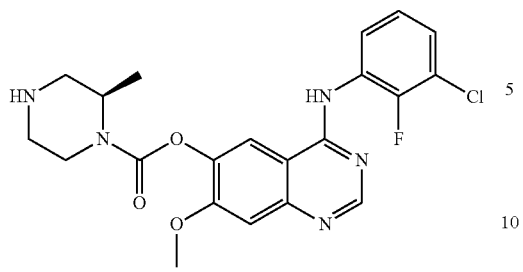

A mixture of Intermediate 9 (8.3 g, 15 mmol) in DCM (100 mL) and HCl/dioxane (10 mL, 4M) was stirred for 30 min at RT. After filtration, the solid was collected and redissolved in water, and then adjusted to pH=8 with saturated NaHCO$_3$. The precipitate was collected and washed with CH$_2$Cl$_2$. The solid was dried under vacuum to give the Intermediate 10 (8 g, 85% purity) as yellow solid. This crude product was used for the next step without purification.

Intermediate 11

(S)-2,4-dimethylpiperazine-1-carbonyl chloride

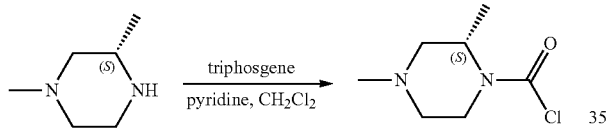

To a solution of triphosgene (1.04 g, 3.5 mmol) in DCM (20 mL) under nitrogen was added pyridine (2.3 g, 28.0 mmol) drop-wise at 0° C. followed by addition of (S)-1,3-dimethylpiperazine (800 mg, 7.0 mmol) in DCM (30 mL), the reaction mixture was warmed to RT and stirred overnight as monitored by TLC(R$_f$=0.9, PE: EtOAc=1:1). The mixture was concentrated to give Intermediate 11 (3 g, crude) which was used without purification.

Intermediate 12

(±)-tert-Butyl (4-(chlorocarbonyl)-3-methylpiperazine-1-carboxylate

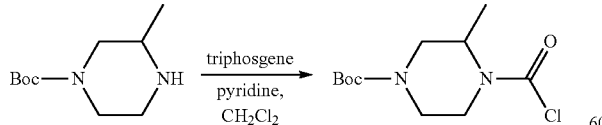

To a mixture of triphosgene (23 g, 75 mmol) in anhydrous DCM (250 mL) was added pyridine (18 g, 225 mmol) drop-wise followed by addition of (±)-tert-butyl 3-methylpiperazine-1-carboxylate (15 g, 75 mmol) at 0° C. The mixture was stirred overnight at RT. TLC showed the starting material was consumed. The mixture was concentrated to afford Intermediate 12 as yellow solid, which was used without further purification.

Intermediate 13

(±)-4-tert-Butyl 1-{4[(2-fluorophenyl)amino]-7-methoxyquinazolin-6-yl}2-methylpiperazine-1,4-dicarboxylate

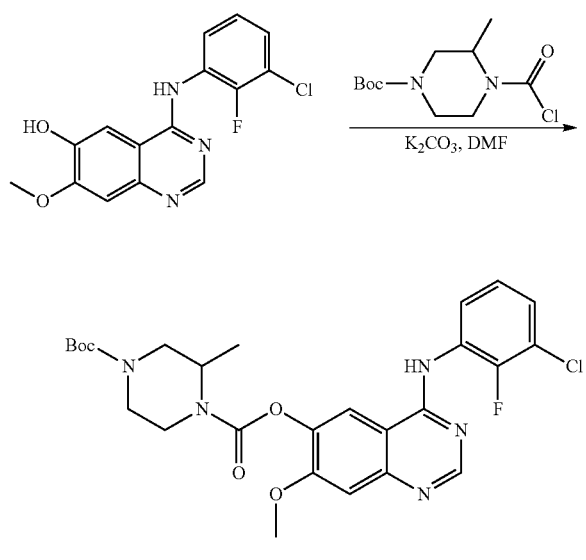

A mixture of Intermediate 7 (19.2 g, 60 mmol), Intermediate 12 prepared according to above procedure and potassium carbonate (16.6 g, 120 mmol) in anhydrous DMF (300 mL) was stirred overnight at RT. The reaction mixture was poured into water (250 mL) and filtered, and the filter cake was dried under vacuum to afford Intermediate 13 (25 g, 75% yield) as yellow solid. HPLC: t$_R$=2.68 min in 10-80AB_6 min chromatography (Ultimate XB-C18, 3.0*50 mm, 3 um). LCMS: t$_R$=0.792 min in 5-95AB_1.5 min chromatography (Welch Xtimate C18, 2.1*30 mm, 3 um), MS (ESI) m/z 546.0 [M+H]$^+$.

Intermediate 14

(±)-4-[(3-Chloro-2-fluorophenyl)amino]-7-methoxyquinazolin-6-yl-2-methylpiperazine-1-carboxylate

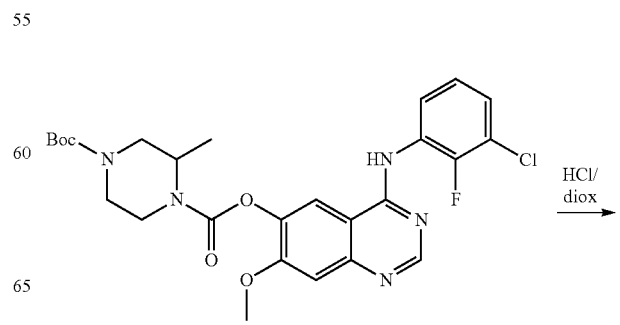

-continued

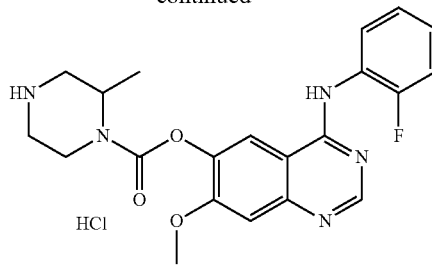

A mixture of Intermediate 13 (25 g, 46 mmol) in a solution of HCl/dioxane (250 mL, 4M) was stirred for 30 min at RT. The resulting solid was collected and redissolved in water, and then adjusted to pH=8 with saturated NaHCO$_3$. The precipitate was collected and washed with CH$_2$Cl$_2$. The solid was dried under vacuum to give the product (19 g, 93% yield) as yellow solid. HPLC: $t_R$=1.58 min in 10-80AB_6 min chromatography (Ultimate XB-C18, 3.0*50 mm, 3 um). LCMS: $t_R$=0.638 min in 5-95AB_1.5 min chromatography (Welch Xtimate C18, 2.1*30 mm, 3 um), MS (ESI) m/z 445.1 [M+H]$^+$. $^1$H NMR (CD$_3$OD 400 MHz): δ 8.44 (s, 1H), 8.08 (s, 1H), 7.60 (t, 1H), 7.39 (t, 1H), 7.27-7.20 (m, 2H), 4.41 (s, 1H), 4.00 (s, 3H), 3.08-2.79 (m, 4H), 1.43 (brs, 3H).

Example 1

4-[(3-Chloro-2-fluorophenyl)amino]-7-methoxyquinazolin-6-yl (2R)-2,4-dimethylpiperazine-1-carboxylate

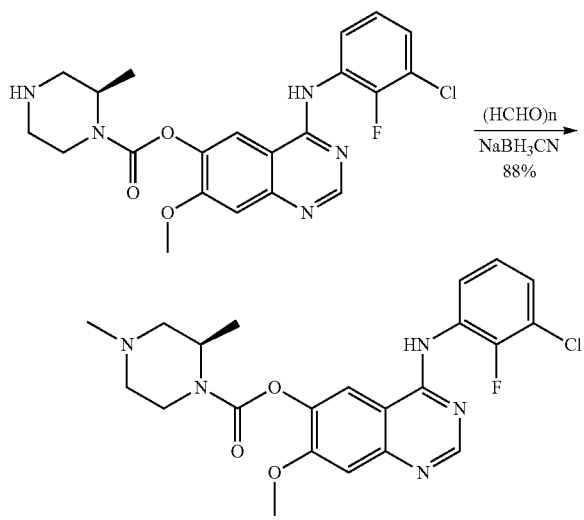

To a mixture of Intermediate 10 (8 g, 15 mmol, 85% purity) and paraformaldehyde (1 g, 32 mmol) in MeOH (100 mL) was added sodium cyanoborohydride (2 g, 32 mmol) and the reaction mixture was stirred at RT overnight. The reaction mixture was concentrated in vacuo, the residue was diluted with water and extracted with EtOAc (3×100 mL). The combined organic layers were washed with brine, dried over anhydrous sodium sulfate and concentrated under reduced pressure. The crude product was purified by reverse phase preparative HPLC (column: synergi 77*250, 10 um, gradient: 5-35% B (A=water/0.05% formic acid, B=acetonitrile), flow rate: 140 mL/min). The fraction contained desired product was neutralized with saturated potassium carbonate and extracted with EtOAc. The combined organic layer was concentrated in vacuo and freeze-dried to afford Example 1 (4 g, 58% yield for 2 steps) as white solid.

LC-MS: $t_R$=1.406 min in 4 min chromatography, MS (ESI) m/z 460.0 [M+H]$^+$

SFC: $t_R$=1.637 min in 3 min chromatography (Chiralpak AD-3 50*4.6 mm I.D, 3 um), MS (ESI) m/z 460.1 [M+H]$^+$ $^1$H NMR (CDCl$_3$ 400 MHz): δ 8.76 (s, 1H), 8.53-8.48 (m, 1H), 7.65 (s, 1H), 7.44 (brs, 1H), 7.34 (s, 1H), 7.19-7.15 (m, 2H), 4.51-4.50 (m, 1H), 4.20-4.05 (m, 1H), 3.99 (s, 3H), 3.50-3.30 (m, 1H), 2.87 (d, 1H), 2.73 (d, 1H), 2.35 (s, 3H), 2.35-2.25 (m, 1H), 2.13-2.11 (m, 1H), 1.47 (s, 3H).

Example 1

Form A

Form A material was produced by heating Example 1 to 140° C. Approximately 10 mg of Example 1 was placed in an aluminium pan. The pan was heated to 140° C. with the heating rate of 10° C./min using differential scanning calorimetry (DSC) and subsequently cooled to RT under nitrogen gas.

Form A material was also produced by slow evaporation of Example 1 in IPA. Approximately 10 mg of Example 1 was weighed to a 3-mL vial, 0.25 mL of IPA was added to dissolve the solid. After evaporating at RT for 24 hours, Example 1 (Form A) was obtained.

Form A material was also produced by slurrying Example 1 in MTBE for 24 hours at 50° C. Approximately 10 mg of Example 1 was weighed to a 3-mL vial, 1 mL of MTBE was added and then the suspension was stirred for 24 hours at 50° C. to obtain Example 1 (Form A) was obtained.

Form A material was also produced by anti-solvent addition of EtOAc/heptane. Approximately 10 mg of Example 1 was weighed to a 5-mL vial, 1 mL of EtOAc was added to dissolve the solid and the 4 mL of anti-solvent heptane was added to the vial slowly. The mixture was stirred for 24 hours at RT to obtain Example 1 (Form A).

The X-ray powder diffraction spectra for Example 1 (Form A) showed the material to be crystalline. The material had a melting point of 192.4° C. (onset).

Example 1

Form E

Approximately 10 mg of Example 1 was weighed to a 5 mL vial, 0.25 mL of THF was added to dissolve the solid, then 4 mL of anti-solvent heptane was added to the vial and the mixture stirred for 24 hours at RT before the solid was isolated. The sample (Form E) was determined to be crystalline by XRPD and had a melting point of 194.2° C. (onset).

Example 1

Form I

Approximately 10 mg of Example 1 was weighed to a 3 mL vial, 1 mL of H$_2$O to was added the vial and the suspension stirred for 24 hours at 50° C. before the solid was isolated. The sample (Form I) was determined to be crystalline by XRPD and had a melting point of 193.3° C. (onset).

Example 1

Form J

Approximately 10 mg of Example 1 was weighed to a 3 mL vial, 1 mL of H₂O was added to the vial and the suspension stirred for 24 hours at RT before the solid was isolated. The sample (Form J) was determined to be crystalline by XRPD and had a melting point of 193.3° C. (onset).

Example 2

4-[(3-Chloro-2-fluorophenyl)amino]-7-methoxyquinazolin-6-yl (2R)-2,4-dimethylpiperazine-1-carboxylate hydrochloride

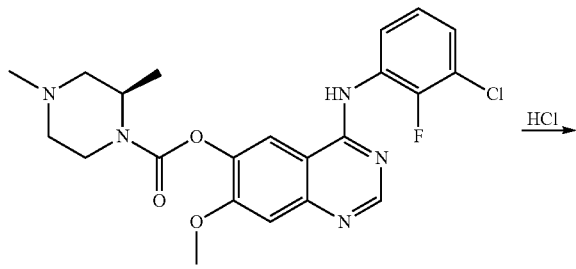

Example 1 (1.8 g) was dissolved in acetonitrile (5 mL), then 1 N HCl (5 mL) was added slowly, the solution was dried by lyophilization to give Example 2 (1.93 g) as a yellow solid. LC-MS: $t_R$=1.355 min in 4 min chromatography, MS (ESI) m/z 460.1 [M+H]⁺. SFC: $t_R$=1.773 min in 3 min chromatography (Chiralpak AD-3 50*4.6 mm I.D, 3 um), MS (ESI) m/z 460.1 [M+H]⁺. ¹H NMR (CD₃OD 400 MHz): δ 8.55 (s, 1H), 8.33-8.16 (m, 1H), 7.56 (t, 1H), 7.45 (t, 1H), 7.33 (s, 1H), 7.28-7.20 (m, 1H), 4.81-4.59 (m, 1H), 4.52-4.15 (m, 1H), 4.10-3.95 (m, 3H), 3.74-3.48 (m, 3H), 3.35 (br. s., 1H), 3.24-3.09 (m, 1H), 2.97 (s, 3H), 1.54 (br. s., 3H). $[\alpha]_D^{25}$=−14.96 (c10, DMSO).

Formation of Example 2 mono-HCl salt Form A₁

To approximately 10 mg of Example 1 was added 0.35 mL of IPA, followed by 0.217 mL of hydrochloric acid. The solution was sealed tightly with a cap and left to stir on a magnetic stirrer plate. During the stirring, some white precipitate was observed. After approximately 24 hours, the sample was separated and dried at RT by vacuum. This form (mono-HCl salt Form A₁) was determined to be crystalline by XRPD and had a melting point of 259.6° C. (onset).

Mono-HCl salt Form A₁ was also produced by reaction crystallization of Example 1 and hydrochloric acid in EtOH at RT. To approximately 10 mg of Example 1, was added 0.35 mL of EtOH to dissolve the solid, then 0.217 mL of hydrochloric acid was added to the solution. The solution was sealed tightly with a cap and left to stir on a magnetic stirrer plate. During the stirring, some white precipitate was observed. After approximately 24 hours, the sample was separated and dried at RT by vacuum. This form (mono-HCl salt Form A₁) was determined to be crystalline by XRPD and had a melting point of 259.6° C. (onset).

Mono-HCl salt Form A₁ was also produced by reaction crystallization of Example 1 and hydrochloric acid in acetone at RT. To approximately 10 mg of Example 1, was added 0.35 mL of acetone to dissolve the solid, followed by 0.217 mL of hydrochloric acid. The solution was sealed tightly with a cap and left to stir on a magnetic stirrer plate. During the stirring, some white precipitate was observed. After approximately 24 hours, the sample was separated and dried at RT by vacuum. This form (mono-HCl salt Form A₁) was determined to be crystalline by XRPD and had a melting point of 259.6° C. (onset).

Mono-HCl salt Form A₁ was also produced by reaction crystallization of Example 1 and hydrochloric acid in THF at RT. To approximately 10 mg of Example 1, was added 0.35 mL of THF to dissolve the solid, then 0.217 mL of hydrochloric acid was added. The solution was sealed tightly with a cap and left to stir on a magnetic stirrer plate. During the stirring, some white precipitate was observed. After approximately 24 hours, the sample was separated and dried at RT by vacuum. This form (mono-HCl salt Form A₁) was determined to be crystalline by XRPD and seen to be different to previously seen forms. This material had a melting point of 259.6° C. (onset).

Example 3

4-[(3-Chloro-2-fluorophenyl)amino]-7-methoxyquinazolin-6-yl (2S)-2,4-dimethylpiperazine-1-carboxylate

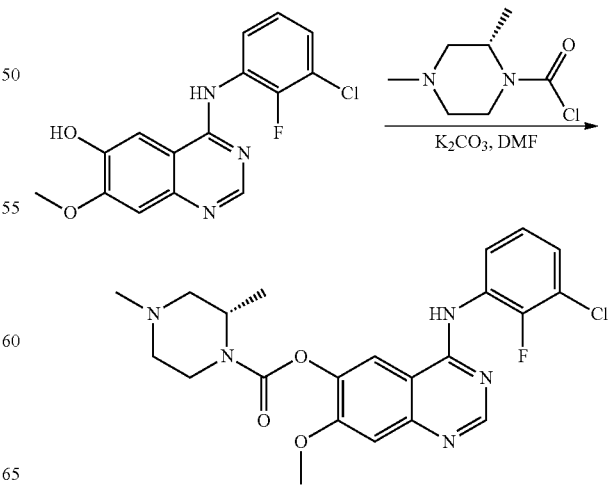

A solution of Intermediate 7 (150 mg, 0.47 mmol), Intermediate 11 (1 g, crude) and K$_2$CO$_3$ (130 mg, 0.94 mmol) in N,N-dimethyl-formamide (10 mL) was stirred at 30° C. overnight as monitored by LCMS. The solution was filtered and purified by reverse phase preparative HPLC (column: ASB 150*25 mm*Sum, gradient: 3-28% B (A=water/0.05% HCl, B=acetonitrile), flow rate: 30 mL/min) to give Example 3 (21.0 mg). LC-MS t$_R$=1.156 min in 4 min chromatography, MS (ESI) m/z 460.0 [M+H]$^+$ SFC: t$_R$=2.084 min in 3 min chromatography (Chiralpak AD-3 50*4.6 mm I.D, 3 um), MS (ESI) m/z 460.1 [M+H]$^+$; $^1$H NMR (CD$_3$OD, 400 MHz): δ 8.77 (s, 1H), 8.43 (s, 1H), 7.57-7.50 (m, 2H), 7.38 (s, 1H), 7.32-7.28 (m, 1H), 4.51-4.21 (m, 1H), 4.10 (s, 3H), 3.77-3.35 (m, 5H), 3.27-3.17 (m, 1H), 2.99 (s, 3H), 1.58-1.49 (m, 3H).

Example 4

4-[(3-Chloro-2-fluorophenyl)amino]-7-methoxyquinazolin-6-yl (±) 2,4-dimethylpiperazine-1-carboxylate

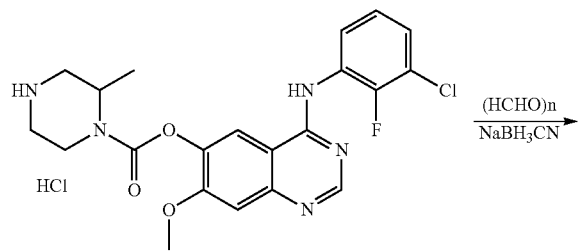

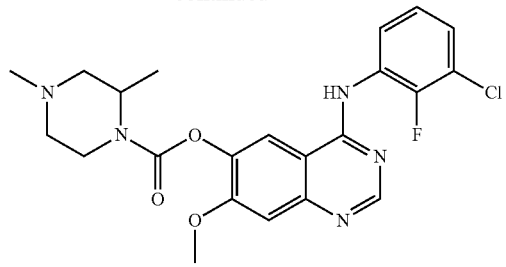

A mixture of Intermediate 14 (1.0 g, 2.0 mmol, 96% purity), paraformaldehyde (200 mg, 6.6 mmol), acetic acid (400 mg, 6.6 mmol) in MeOH (15 mL) was stirred for 2 hours at RT. Sodium cyanoborohydride (400 mg, 6.6 mmol) was added. The resulting reaction mixture was stirred for another 2 hours. The mixture was worked up and purified by reverse phase preparative HPLC (column: ASB, gradient: 5-30% B (A=water/0.05% HCl, B=acetonitrile), flow rate: 30 mL/min) to afford Example 4 (300 mg, 27%) as white solid. LC-MS t$_R$=1.099 min in 4 min chromatography, MS (ESI) m/z 460.1 [M+H]$^+$; $^1$H NMR (CD$_3$OD 400 MHz): δ 8.79 (s, 1H), 8.51 (s, 1H), 7.58-7.52 (dd, 2H), 7.45 (s, 1H), 7.34-7.30 (t, 1H), 4.71-4.30 (m, 2H), 4.13 (s, 3H), 3.75-3.58 (m, 3H), 3.55-3.42 (m, 1H), 3.27 (s, 1H), 3.02 (s, 3H), 1.62-1.53 (m, 3H).

Example 5

Alternative crystalline forms of 4-[(3-chloro-2-fluorophenyl)amino]-7-methoxyquinazolin-6-yl (2R)-2,4-dimethylpiperazine-1-carboxylate

| Freebase Form | Preparation Methods | XRPD Angle 2-Theta (2θ) | XRPD Intensity (%) | Melting point (° C.) |
|---|---|---|---|---|
| Form A | Amorphous freebase heated to 135° C. (10° C./min) Slow evaporation: IPA, iPrOAc Slurry in heptane, MTBE, DCM/heptane (1/4, v/v), THF/heptane (1/4, v/v), iPrOAc/heptane (1/4, v/v) at RT Slurry in heptane, MTBE, acetone/H$_2$O (1/4, v/v), MeOH/H$_2$O (1/4, v/v), EtOH/H$_2$O (1/4, v/v), THF/H$_2$O (1/4, v/v), DCM/heptane (1/4, v/v), THF/heptane (1/4, v/v), iPrOAc/heptane (1/4, v/v), EtOH/heptane (1/4, v/v) at 50° C. Anti-solvent addition (solvent/anti-solvent): EtOAc/heptane, DCM/heptane Wet grinding: acetone, EtOAc | 23.3, 14.3, 9.4 | 100.00, 83.70, 78.08 | 192.4 |
| Form B | Slurry in acetone/H$_2$O (1/4, v/v), MeOH/H$_2$O (1/4, v/v), EtOH/H$_2$O (1/4, v/v), THF/H$_2$O (1/4, v/v) at RT Anti-solvent addition (solvent/anti-solvent): MeOH/H$_2$O, THF/H$_2$O, Dioxane/H$_2$O Wet grinding: EtOH/H$_2$O (1/1, v/v) | 6.3, 3.1, 12.6 | 100.00, 52.07, 35.29 | N/A |
| Form C | Slow evaporation: THF Anti-solvent addition (solvent/anti-solvent): dioxane/heptane | 15.6, 8.6, 13.9 | 100.00, 60.20, 34.59 | N/A |
| Form D | Slow evaporation: EtOH Slurry in EtOH/heptane (1/4, v/v) at RT Anti-solvent addition (solvent/anti-solvent): EtOH/MTBE | 7.3, 11.4, 21.0 | 100.00, 39.48, 23.59 | N/A |
| Form E | Anti-solvent addition (solvent/anti-solvent): THF/heptane | 7.3, 13.7, 13.4 | 100.00, 81.83, 74.07 | 93.0 |
| Form F | Slow evaporation: acetone | 9.3, 16.0, 21.6 | 100.00, 69.50, 57.55 | N/A |

-continued

| Freebase Form | Preparation Methods | XRPD Angle 2-Theta (2θ) | XRPD Intensity (%) | Melting point (° C.) |
|---|---|---|---|---|
| Form G | Slow evaporation: acetone<br>Wet grinding: DCM | 5.1, 7.2, 17.0 | 100.00, 12.14, 8.13 | N/A |
| Form H | Slow evaporation: MeOH<br>Wet grinding: MeOH | 7.7, 21.2, 19.5 | 100.00, 41.70, 39.40 | N/A |
| Form I | Slurry in H$_2$O at 50° C. | 3.5, 7.0, 9.5 | 100.00, 41.22, 32.57 | 193.3 |
| Form J | Slurry in H$_2$O at RT | 7.8, 7.0, 4.9 | 100.00, 49.36, 45.57 | N/A |

Example 6

Alternative salt forms of 4-[(3-chloro-2-fluorophenyl)amino]-7-methoxyquinazolin-6-yl (2R)-2,4-dimethylpiperazine-1-carboxylate

| Salt Form | Preparation Methods | XRPD Angle 2-Theta (2θ) | XRPD Intensity (%) | Melting point (° C.) |
|---|---|---|---|---|
| HCl salt Form A$_1$ | Reaction crystallization of the freebase and hydrochloric acid in IPA, EtOH, acetone or THF at RT | 12.3, 13.9, 9.3 | 100.00, 40.45, 29.34 | 259.6 |
| HCl salt Form B$_1$ | Reaction crystallization of the freebase and hydrochloric acid in EtOH/H$_2$O (v/v, 19/1) at RT, then evaporation | 6.6, 13.2, 12.6 | 100.00, 52.30, 38.68 | N/A |
| Sulfate Form A$_2$ | Reaction crystallization of the freebase and sulfuric acid in IPA at RT | 19.8, 20.4, 22.3 | 100.00, 36.69, 26.58 | N/A |
| Sulfate Form B$_2$ | Reaction crystallization of the freebase and sulfuric acid in EtOH, acetone, THF or EtOH/H$_2$O (v/v, 19/1) at RT | 7.2, 16.7, 14.5 | 100.00, 68.32, 45.68 | 223.7 |
| Phosphate Form A$_3$ | Reaction crystallization of the freebase and phosphoric acid in EtOH at RT | 7.0, 16.5, 22.4 | 100.0, 61.81, 29.12 | 206.0 |
| Phosphate Form B$_3$ | Reaction crystallization of the freebase and phosphoric acid in EtOH/H$_2$O (v/v, 19/1) at RT | 5.1, 23.4, 11.9 | 100.00, 18.27, 16.19 | 177.8 |
| Maleate Form A$_4$ | Reaction crystallization of the freebase and maleic acid in IPA at RT<br>Reaction crystallization of the freebase and maleic acid in acetone at RT, then evaporation | 4.9, 6.6, 12.6 | 100.00, 93.00, 30.51 | 108.1 |
| Maleate Form B$_4$ | Reaction crystallization of the freebase and maleic acid in DCM or THF at RT | 6.7, 4.5, 20.2 | 100.00, 26.67, 11.01 | 120.0 |
| Maleate Form C$_4$ | Reaction crystallization of the freebase and maleic acid in EtOH/H$_2$O (v/v, 19/1) at RT, then evaporation | 6.3, 8.5, 10.6 | 100.00, 87.86, 63.25 | N/A |
| Tartrate Form A$_5$ | Reaction crystallization of the freebase and tartaric acid in EtOH or EtOH/H$_2$O (v/v, 19/1) at RT | 13.3, 6.6, 17.6 | 100.00, 63.41, 49.61 | 158.5 |
| Fumarate Form A$_6$ | Reaction crystallization of the freebase and fumaric acid in acetone at RT<br>Reaction crystallization of the freebase and fumaric acid in IPA at RT, then evaporation | 6.6, 5.2, 20.4 | 100.00, 51.69, 29.49 | 212.8 |
| Fumarate Form B$_6$ | Reaction crystallization of the freebase and fumaric acid in DCM at RT | 9.3, 9.8, 26.7 | 100.00, 58.74, 54.18 | 205.8 |
| Fumarate Form C$_6$ | Reaction crystallization of the freebase and fumaric acid in EtOH/H$_2$O (v/v, 19/1) at RT, then evaporation | 7.2, 17.0, 6.2 | 100.00, 86.58, 54.86 | 199.2 |
| Citrate Form A$_7$ | Reaction crystallization of the freebase and citric acid in DCM at RT | 28.3, 15.2, 22.2 | 100.00, 36.42, 26.50 | 157.9 |
| Succinate | Reaction crystallization of the | 6.5, 17.7, | 100.00, 31.30, | 191.8 |

-continued

| Salt Form | Preparation Methods | XRPD Angle 2-Theta (2θ) | XRPD Intensity (%) | Melting point (° C.) |
|---|---|---|---|---|
| salt Form $A_8$ | freebase and succinic acid in acetone, DCM or EtOAc at RT Reaction crystallization of the freebase and succinic acid in EtOH at RT, then evaporation | 14.7 | 24.91 | |
| Succinate salt Form $B_8$ | Reaction crystallization of the freebase and succinic acid in acetone/$H_2O$ (v/v, 19/1) at RT, then evaporation | 6.0, 24.3, 8.3 | 100.00, 70.58, 62.41 | N/A |
| Adipate Form $A_9$ | Reaction crystallization of the freebase and adipic acid in DCM at RT Reaction crystallization of the freebase and adipic acid in acetone or EtOAc at RT, then evaporation | 5.0, 8.5, 16.6 | 100.00, 9.38, 6.46 | 133.4 |
| Adipate Form $B_9$ | Reaction crystallization of the freebase and adipic acid in EtOH at RT, then evaporation | 4.4, 6.2, 15.7 | 100.00, 43.19, 36.16 | N/A |
| Mesylate Form $A_{10}$ | Reaction crystallization of the freebase and methanesulfonic acid in acetone at RT | 13.1, 16.9, 7.2 | 100.0, 72.46, 63.66 | N/A |
| Mesylate Form $B_{10}$ | Reaction crystallization of the freebase and methanesulfonic acid in DCM or EtOAc at RT | 18.6, 23.0, 19.3 | 100.00, 94.62, 86.41 | 224.0 |
| Malonate Form $A_{11}$ | Reaction crystallization of the freebase and malonic acid in DCM or EtOAc at RT Reaction crystallization of the freebase and malonic acid in acetone or EtOH at RT, then evaporation | 15.0, 13.1, 10.2 | 100.00, 65.81, 50.20, | 157.7 |
| Benzoate Form $A_{12}$ | Reaction crystallization of the freebase and benzoic acid in acetone, THF, EtOH, DCM or acetone/$H_2O$ (v/v, 19/1) at RT, then evaporation | 5.9, 17.0, 3.7 | 100.00, 38.62, 22.28 | N/A |
| Benzoate Form $B_{12}$ | Reaction crystallization of the freebase and benzoic acid in EtOAc at RT, then evaporation | 6.0, 26.3, 25.9 | 100.00, 56.07, 47.79 | N/A |

Example 7

4-[(3-Chloro-2-fluorophenyl)amino]-7-methoxyquinazolin-6-yl (2R)-2,4-dimethylpiperazine-1-carboxylate succinate

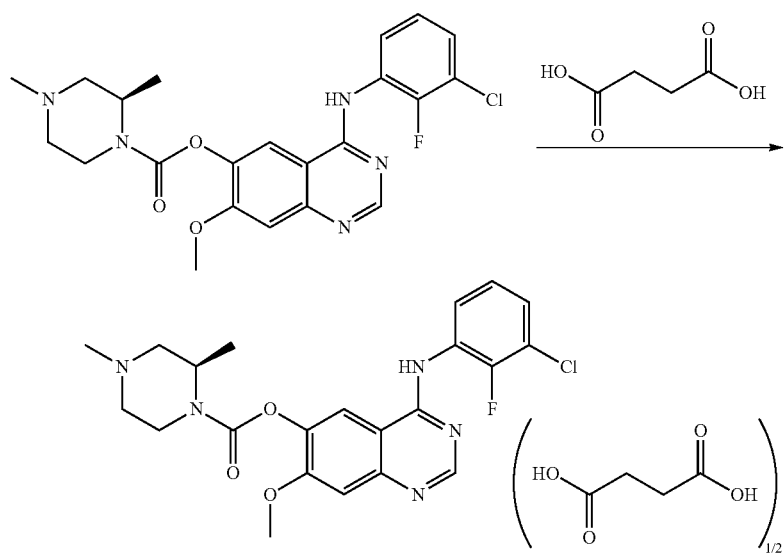

Example 1 (10 mg, 0.022 mmol) was dissolved in 0.44 mL of acetone in a vial. Succinic acid (2.57 mg, 0.022 mmol) was added to the solution. The resulting mixture was sealed tightly with a cap and allowed to stir on a magnetic stirrer plate. During the stirring, some white precipitate was observed. After approximately 24 hours, the white solid was separated and dried at room temperature under vacuum. $^1$H NMR (400 MHz, DMSO-$d_6$) 9.74 (s, 1H), 8.47 (s, 1H), 8.22 (s, 1H), 7.51-7.47 (m, 2H), 7.34 (s, 1H), 7.30-7.26 (m, 1H), 4.4-4.2 (br, 1H), 3.95 (s, 3H), 3.9-3.7 (br, 1H), 2.82-2.80 (d, 1H), 2.70-2.67 (s, 1H), 2.42 (s, 2H), 2.21 (s, 3H), 2.12-2.10 (m, 1H), 1.94-1.89 (m, 1H), 1.34 (s, 3H).

Formation of Example 7 Succinate salt Form $A_8$

Succinate salt Form $A_8$ was produced by the procedure described above. This form (Succinate salt Form $A_8$) was determined to be crystalline by XRPD and had a melting point of 191.8° C. (onset).

Succinate salt Form $A_8$ was also produced by reaction crystallization of Example 1 and succinic acid in EtOH at RT. To approximately 10 mg of Example 1, was added 0.59 mL of EtOH to dissolve the solid, then 2.57 mg of succinic acid was added to the solution. The solution was sealed tightly with a cap and left to stir on a magnetic stirrer plate. After approximately 24 hours stirring, the solution was evaporated to dryness at RT. This form (Succinate salt Form $A_8$) was determined to be crystalline by XRPD and had a melting point of 191.8° C. (onset).

Succinate salt Form $A_8$ was also produced by reaction crystallization of Example 1 and succinic acid in DCM at RT. To approximately 10 mg of Example 1, was added 0.25 mL of DCM to dissolve the solid, then 2.57 mg of succinic acid was added. The solution was sealed tightly with a cap and left to stir on a magnetic stirrer plate. During the stirring, some white precipitate was observed. After approximately 24 hours, the sample was separated and dried at RT by vacuum. This form (Succinate salt Form $A_8$) was determined to be crystalline by XRPD and had a melting point of 191.8° C. (onset). Succinate salt Form $A_8$ was also produced by reaction crystallization of Example 1 and succinic acid in EtOAc at RT. To approximately 10 mg of Example 1, was added 0.25 mL of EtOAc to dissolve the solid, then 2.57 mg of succinic acid was added. The solution was sealed tightly with a cap and left to stir on a magnetic stirrer plate. During the stirring, some white precipitate was observed. After approximately 24 hours, the sample was separated and dried at RT by vacuum. This form (Succinate salt Form $A_8$) was determined to be crystalline by XRPD and had a melting point of 191.8° C. (onset).

The invention claimed is:

1. A compound which is 4-[(3-chloro-2-fluorophenyl)amino]-7-methoxyquinazolin-6-yl (2R)-2,4-dimethylpiperazine-1-carboxylate, or a pharmaceutically acceptable salt thereof.

2. The pharmaceutically acceptable salt of the compound as claimed in claim 1.

3. The compound, or a pharmaceutically acceptable salt thereof, as claimed in claims 1 or 2, in crystalline form.

4. A pharmaceutical composition comprising a compound, or a pharmaceutically acceptable salt thereof, as claimed in claims 1, 2 and 3, in association with a pharmaceutically-acceptable diluent or carrier.

5. The compound, or a pharmaceutically acceptable salt thereof, according to claims 1, 2 and 3, in combination with an anti-tumour agent selected from:

(i) an anti-CTLA-4 antibody;
(ii) 6-(4-bromo-2-chloro-phenylamino)-7-fluoro-3-methyl-3H-benzoimidazole-5-carboxylic acid (2-hydroxyethoxy)-amide or a pharmaceutically acceptable salt thereof;
(iii) 1-[(1S)-1-(imidazo[1,2-a]pyridin-6-yl)ethyl]-6-(1-methyl-1H-pyrazol-4-yl)-1H-[1,2,3]triazolo[4,5-b]pyrazine or a pharmaceutically acceptable salt thereof;
(iv) an anti-PD-1 antibody; or
(v) an 0040 antibody.

6. 4-[(3-chloro-2-fluorophenyl)amino]-7-methoxyquinazolin-6-yl (2R)-2,4-dimethylpiperazine-1-carboxylate.

7. The 4-[(3-chloro-2-fluorophenyl)amino]-7-methoxyquinazolin-6-yl (2R)-2,4-dimethylpiperazine-1-carboxylate, as claimed in claim 6, in crystalline form.

8. A pharmaceutical composition comprising 4-[(3-chloro-2-fluorophenyl)amino]-7-methoxyquinazolin-6-yl (2R)-2,4-dimethylpiperazine-1-carboxylate as claimed in claim 6 or 7, in association with a pharmaceutically-acceptable diluent or carrier.

9. The 4-[(3-chloro-2-fluorophenyl)amino]-7-methoxyquinazolin-6-yl (2R)-2,4-dimethylpiperazine-1-carboxylate as claimed in claim 6 or 7, in combination with an anti-tumour agent selected from:

(i) an anti-CTLA-4 antibody;
(ii) 6-(4-bromo-2-chloro-phenylamino)-7-fluoro-3-methyl-3H-benzoimidazole-5-carboxylic acid (2-hydroxyethoxy)-amide or a pharmaceutically acceptable salt thereof;
(iii) 1-[(1S)-1-(imidazo[1,2-a]pyridin-6-yl)ethyl]-6-(1-methyl-1H-pyrazol-4-yl)-1H-[1,2,3]triazolo[4,5-b]pyrazine or a pharmaceutically acceptable salt thereof;
(iv) an anti-PD-1 antibody; or
(v) an 0040 antibody.

10. 4-[(3-chloro-2-fluorophenyl)amino]-7-methoxyquinazolin-6-yl (2R)-2,4-dimethylpiperazine-1-carboxylate hydrochloride.

11. The 4-[(3-chloro-2-fluorophenyl)amino]-7-methoxyquinazolin-6-yl (2R)-2,4-dimethylpiperazine-1-carboxylate hydrochloride, as claimed in claim 10, in crystalline form.

12. The crystalline form of 4-[(3-chloro-2-fluorophenyl)amino]-7-methoxyquinazolin-6-yl (2R)-2,4-dimethylpiperazine-1-carboxylate hydrochloride as claimed in claim 11 which is 4-[(3-chloro-2-fluorophenyl)amino]-7-methoxyquinazolin-6-yl (2R)-2,4-dimethylpiperazine-1-carboxylate monohydrochloride.

13. The crystalline form of 4-[(3-chloro-2-fluorophenyl)amino]-7-methoxyquinazolin-6-yl (2R)-2,4-dimethylpiperazine-1-carboxylate monohydrochloride as claimed in claim 12 which has an X-ray powder diffraction pattern with specific peaks at about 2-theta=12.3, 13.9, 9.3, 23.3, 18.7, 16.0, 24.6, 26.8 and 28.0°.

14. The crystalline form of 4-[(3-chloro-2-fluorophenyl)amino]-7-methoxyquinazolin-6-yl (2R)-2,4-dimethylpiperazine-1-carboxylate monohydrochloride as claimed in claim 12 which has an X-ray powder diffraction pattern with at least two specific peaks at about 2-theta=12.3° and 13.9°.

15. A pharmaceutical composition comprising 4-[(3-chloro-2-fluorophenyl)amino]-7-methoxyquinazolin-6-yl (2R)-2,4-dimethylpiperazine-1-carboxylate hydrochloride as claimed in claims 10-13 and 14, in association with a pharmaceutically-acceptable diluent or carrier.

16. The 4-[(3-chloro-2-fluorophenyl)amino]-7-methoxyquinazolin-6-yl (2R)-2,4-dimethylpiperazine-1-carboxylate hydrochloride as claimed in claims 10-13 and 14, in combination with an anti-tumour agent selected from:
  (i) an anti-CTLA-4 antibody;
  (ii) 6-(4-bromo-2-chloro-phenylamino)-7-fluoro-3-methyl-3H-benzoimidazole-5-carboxylic acid (2-hydroxy-ethoxy)-amide or a pharmaceutically acceptable salt thereof;
  (iii) 1-[(1S)-1-(imidazo[1,2-a]pyridin-6-yl)ethyl]-6-(1-methyl-1H-pyrazol-4-yl)-1H-[1,2,3]triazolo[4,5-b]pyrazine or a pharmaceutically acceptable salt thereof;
  (iv) an anti-PD-1 antibody; or
  (v) an 0040 antibody.

\* \* \* \* \*